(12) United States Patent
DiRusso et al.

(10) Patent No.: US 8,410,118 B2
(45) Date of Patent: Apr. 2, 2013

(54) INHIBITORS OF FATTY ACID UPTAKE AND METHODS OF USE

(75) Inventors: Concetta DiRusso, Lincoln, NE (US); Paul Black, Lincoln, NE (US)

(73) Assignee: NUtech Ventures, Lincoln, NE (US)

( * ) Notice: Subject to any disclaimer, the term of this patent is extended or adjusted under 35 U.S.C. 154(b) by 0 days.

(21) Appl. No.: 13/571,632

(22) Filed: Aug. 10, 2012

(65) Prior Publication Data

US 2012/0302585 A1 Nov. 29, 2012

Related U.S. Application Data

(63) Continuation of application No. 12/791,323, filed on Jun. 1, 2010, now Pat. No. 8,263,640.

(60) Provisional application No. 61/217,498, filed on Jun. 1, 2009.

(51) Int. Cl.

| | | |
|---|---|---|
| *A01N 43/90* | (2006.01) | |
| *A01N 43/54* | (2006.01) | |
| *A01N 43/56* | (2006.01) | |
| *A61K 31/519* | (2006.01) | |
| *A61K 31/505* | (2006.01) | |
| *A61K 31/415* | (2006.01) | |

(52) U.S. Cl. .................. 514/259.5; 514/259.3; 514/269; 514/406

(58) Field of Classification Search ........................ None
See application file for complete search history.

(56) References Cited

U.S. PATENT DOCUMENTS

| | | | |
|---|---|---|---|
| 6,348,321 | B1 | 2/2002 | Stahl et al. |
| 7,070,944 | B2 | 7/2006 | Black et al. |
| 8,263,640 | B2 | 9/2012 | DiRusso et al. |

OTHER PUBLICATIONS

Ansel Introduction to Pharmaceutical Dosage Forms, Fourth Edition 1985, 126.
Arias-Barrau et al., "Methods to monitor Fatty Acid transport proceeding through vectorial acylation," *Methods Mol. Biol.*, 2009, 580:233-249.
Blackburn et al., "Identification and characterization of 4-aryl-3,4-dihydropyrimidin-2(1H)-ones as inhibitors of the fatty acid transporter FATP4," *Bioorganic & Medicinal Chemistry Letters*, 2006, 16:3504-3509.
Bradford, "A rapid and sensitive method for the quantitation of microgram quantities of protein utilizing the principle of protein-dye binding," *Analytical Biochemistry*, 1976, 72(1-2):248-254.
Chiu et al., "Transgenic Expression of Fatty Acid Transport Protein 1 in the Heart Causes Liptocis Cardiomyopathy," *Circulation Research*, 2004, 96:225-233.
Dole, "A relation between non-esterified fatty acids in plasma and the metabolism of glucose," *J. Clin. Invest.*, 1956, 35(2):150-154.
Fogh et al., "One hundred and twenty-seven cultured human tumor cell lines producing tumors in nude mice," *J. Natl. Cancer Inst.*, 1977, 59(1):221-226.
Folch et al., "A Simple Method for the Isolation and Purification of Total Lipides From Animal Tissues," *J. Biol. Chem.*, 1957, 226:497-509.
Grasset et al., "Epithelial properties of human colonic carcinoma cell line Caco-2: electrical parameters," *Am. J. Physiol.*, 1984, 247:C260-267.
Guo et al., "Fatty acid transport and metabolism in HepG2 cells," *Am. J. Physiol. Gastrointest. Liver Physiol.*, 2006, 209:G528-G534.
Hilgers et al., "Caco-2 cell monolayers as a model for drug transport across the intestinal mucosa," *Pharm. Res.*, 1990, 7(9):902-910.
Kim et al., "Inactivation of fatty acid transport protein 1 prevents fat-induced insulin resistance in skeletal muscle," *J. of Clinical Investigation*, 2004, 113(5):756-763.
Li et al. "High-throughput screening for fatty acid uptake inhibitors in humanized yeast identifies atypical antipsychotic drugs that cause dyslipidemias," *J. Lipid Res.*, 2008, 49:230-244.
Li et al., "A live-cell high-throughput screening assay for identification of fatty acid uptake inhibitors," *Anal. Biochem.*, 2005, 336:11-19.
Mosmann, "Rapid colorimetric assay for cellular growth and survival: application to proliferation and cytotoxicity assays," *J. Immunol. Methods*, 1983, 65(1-2):55-63.
Neidle, *Cancer Drug Design and Discovery*, Elsevier/Academic Press, 2008, pp. 427-431.
Sabah et al., "Role of albumin as a fatty acid carrier for biosynthesis of lens lipids," *Exp. Eye Res.*, 2005, 80:31-36.
Sandoval et al., "Fatty acid transport and activation and the expression patterns of genes involved in fatty acid trafficking," *Arch. Biochem. Biophys.*, 2008, 477(2):363-371.
Sealls et al., "Dietary polyunsaturated fatty acids (C18:2 ω6 and C18:3 ω3) do not suppress hepatic lipogenesis," *Biochim. Biophys. Acta*, 2008, 1781:406-414.
Shim et al., "Fatty acid transport protein 4 is dispensable for intestinal lipid absorption in mice," *J. Lipid Res.*, 2009, 50:491-500.
Stafford & Morse, "Chromatin Remodeling by Transcriptional Activation Domains in a Yeast Episome," *J. Biol. Chem.*, 1997, 272:11526-11534.
Student et al., "Induction of Fatty Acid Synthetase Synthesis in Differentiati3nTg3—L1 Preadipocytes," *J. Biol. Chem.*, 1980, 255:4745-4750.
Wu et al., "FATP1 is an Insulin-Sensitive Fatty Acid Transporter Involved in Diet-Induced Obesity," *Molecular and Cellular Bio.*, 2006, 26(9):3455-3467.
Yamada et al., "Measurement of Glucose Uptake and Intracellular Calcium Concentration in Single, Living Pancreatic β-Cells," *J. Biol. Chem.*, 2000, 275:22278-22283.
Zou et al., "Vectorial acylation in *Saccharomyces cerevisiae*," *J. Biol. Chem.*, 2003, 278:16414-16422.

*Primary Examiner* — James D Anderson
*Assistant Examiner* — Stephanie Springer
(74) *Attorney, Agent, or Firm* — Fish & Richardson P.C.

(57) ABSTRACT

The present disclosure describes inhibitors of fatty acid uptake and methods of using such inhibitors. Specifically, the present disclosure describes inhibitors with specificity for FATP2.

9 Claims, 7 Drawing Sheets

INHIBITORS OF FATTY ACID UPTAKE AND METHODS OF USE

CROSS REFERENCE TO RELATED APPLICATIONS

This application is a continuation application under 35 U.S.C. §120 of U.S application Ser. No. 12/791,323, filed Jun. 1, 2010, which claims benefit under 35 U.S.C. 119(e) to U.S. Application No. 61/217,498, filed on Jun. 1, 2009.

FEDERALLY SPONSORED RESEARCH OR DEVELOPMENT

This invention was made with government support under Grant No. D071076 awarded by the National Institutes of Health. The government has certain rights in the invention.

TECHNICAL FIELD

This disclosure generally relates to inhibitors of fatty acid uptake.

BACKGROUND

It is becoming increasingly apparent that typical western diets high in fat lead to a plethora of pathophysiological states ranging from obesity and type 2 diabetes to coronary heart disease. The correlation between chronically elevated plasma free fatty acids and triglycerides with the development of obesity, insulin resistance and cardiovascular disease has led to the hypothesis that decreases in pancreatic insulin production, cardiac failure, arrhythmias, and hypertrophy are due to aberrant accumulation of lipids in these tissues that normally do not store significant levels of fatty acids and triglycerides.

SUMMARY

The present disclosure describes inhibitors of fatty acid uptake and methods of using such inhibitors.

Described herein is a method of inhibiting fatty acid uptake by cells, such as intestinal epithelial cells and hepatocytes. The method can include contacting the cells with an inhibitor as provided herein. In one embodiment, the inhibitor is a compound of Formula (I):

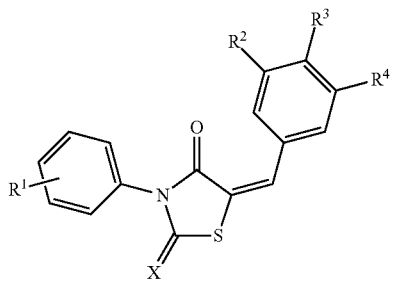

or a pharmaceutically acceptable salt form thereof, wherein:
X is O or S;
$R^1$ is selected from the group consisting of: F, Cl, Br, I, OH, and $O(C_{1-6}$ alkyl);
$R^2$, $R^3$, and $R^4$ are independently selected from the group consisting of: H, F, Cl, Br, I, OH, and $O(C_{1-6}$ alkyl), wherein at least two of $R^2$, $R^3$, and $R^4$ are not H.

In some embodiments, X is S. In some embodiments, $R^1$ is selected from the group consisting of: F, Cl, and $O(C_{1-6}$ alkyl). In some embodiments, $R^2$ is selected from H and Br. In some embodiments, $R^3$ is OH. In some embodiments, $R^4$ is $O(C_{1-6}$ alkyl).

Non-limiting examples of a compound of Formula (I) include:

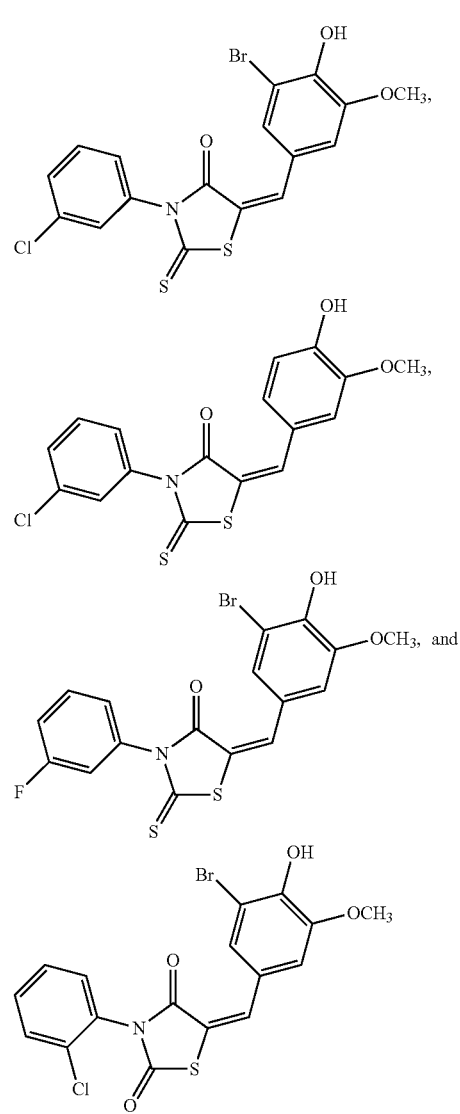

or a pharmaceutically acceptable salt form thereof.

In another embodiment, an inhibitor as described herein is a compound of Formula

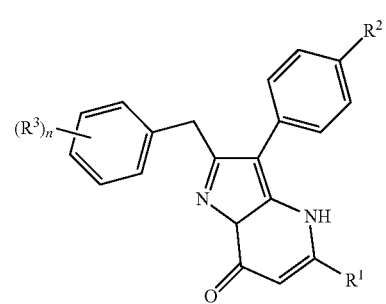

or a pharmaceutically acceptable salt form thereof, wherein:
$R^1$ is H or $NO_2$;
$R^2$ is selected from the group consisting of: H, F, Cl, Br, I, OH, and $O(C_{1-6}$ alkyl);
$R^3$ is selected from the group consisting of: F, Cl, Br, I, OH, and $O(C_{1-6}$ alkyl); and
n is an integer from 0 to 5.

In some embodiments, $R^1$ is $NO_2$. In some embodiments, $R^2$ is selected from the group consisting of: H, Cl, and $O(C_{1-6}$ alkyl). In some embodiments, n is 0.

Non-limiting examples of a compound of Formula (II) include:

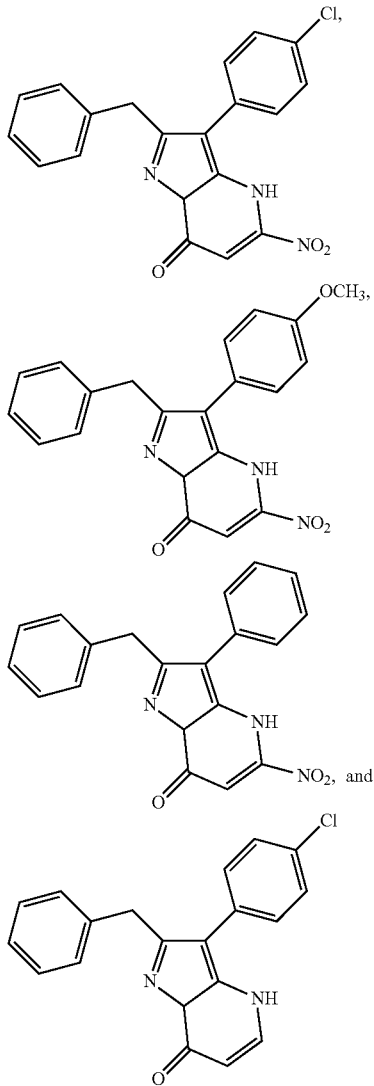

or a pharmaceutically acceptable salt form thereof.

In some embodiments, an inhibitor as provided herein is a compound of Formula (III):

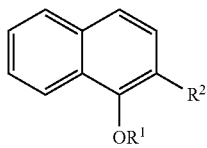

or a pharmaceutically acceptable salt form thereof, wherein:
$R^1$ is H or $O(C_{1-6}$ alkyl); and
$R^2$ is a substituted or unsubstituted heterocycloalkyl or heteroaryl.

In some embodiments, $R^1$ is H. In some embodiments, $R^2$ is a substituted or unsubstituted heterocylcoalkyl.

Non-limiting examples of a compound of Formula (III) include:

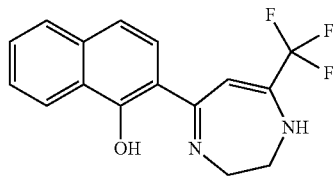 [SMILES: Oc1c(C2=NCCNC(C(F)(F)F)=C2)ccc2ccccc12]

or a pharmaceutically acceptable salt form thereof.

Further provided herein are inhibitors selected from a compound of Formula (IV):

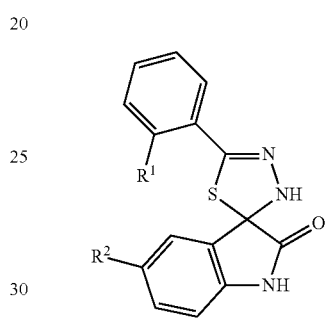

or a pharmaceutically acceptable salt form thereof, wherein:
$R^1$ and $R^2$ are independently selected from the group consisting of: H, F, Cl, Br, I, OH, and $O(C_{1-6}$ alkyl).

In some embodiments, $R^1$ is selected from H and OH. In some embodiments, $R^2$ is selected from H and Br.

Non-limiting examples of a compound of Formula (IV) includes:

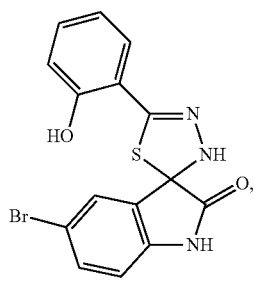

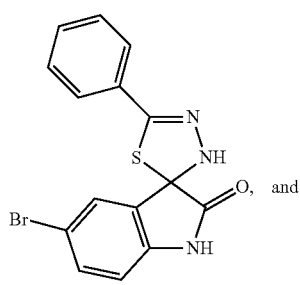

-continued

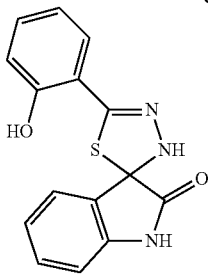

or a pharmaceutically acceptable salt form thereof.

In some embodiments, an inhibitor as provided herein is a compound:

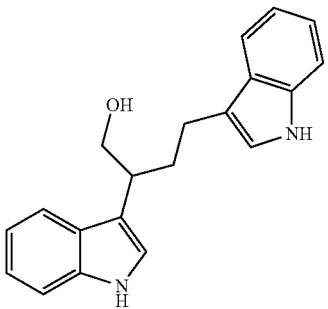 [SMILES: OCC(CCc1c[nH]c2ccccc12)c1c[nH]c2ccccc12]

or a pharmaceutically acceptable salt form thereof.

Also provided herein is a method of treating a disease, comprising:
administering, to an individual, an inhibitor as described herein. In some embodiments, the disease being treated can include obesity, metabolic syndrome, insulin resistant diabetes, cardiovascular disease, stroke, gallbladder disease, osteoarthritis, sleep apnea, respiratory problems and cancer.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DESCRIPTION OF DRAWINGS

Like reference symbols in the various drawings indicate like elements.

DETAILED DESCRIPTION

Figure 1:
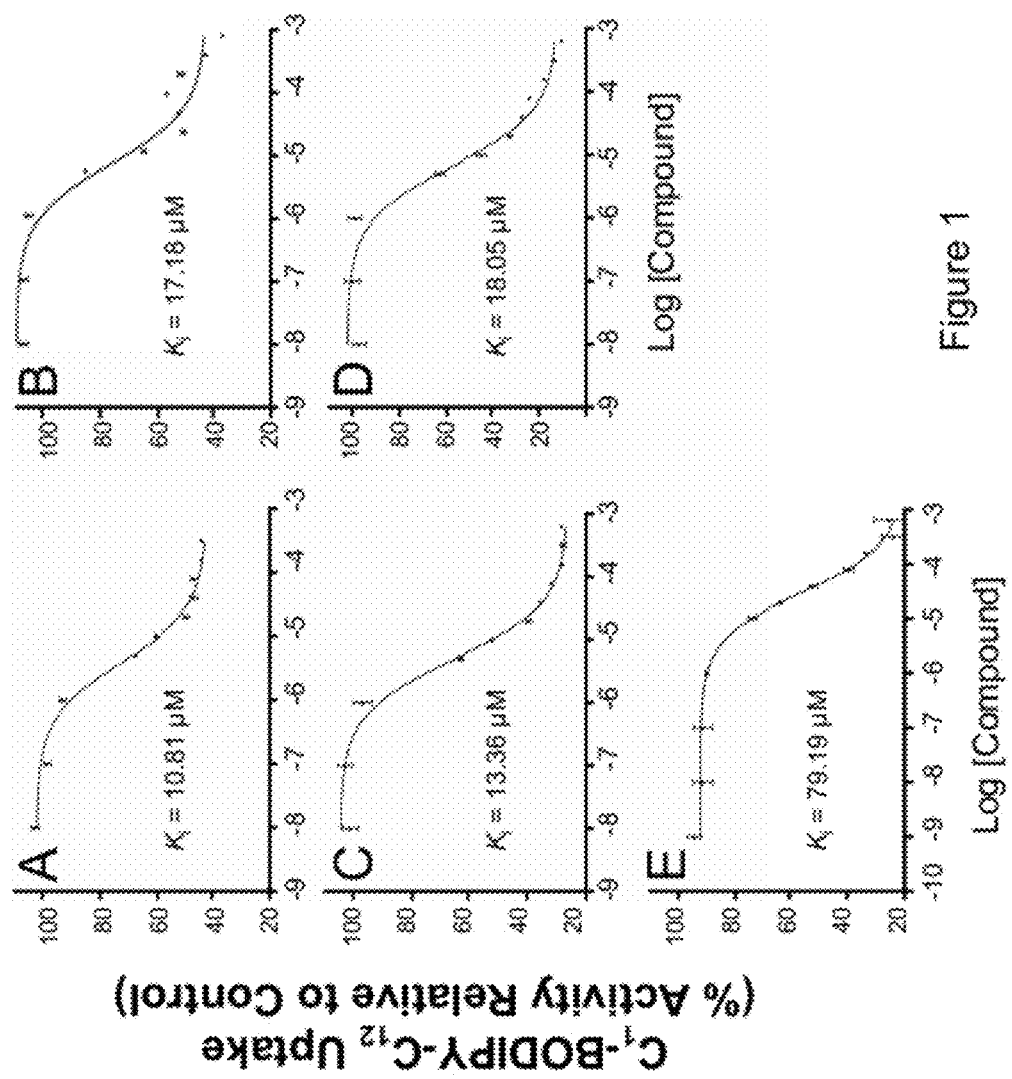
FIG. 1 shows that the titration of selected compounds yields sigmoidal dose-response curves for the inhibition of $C_1$-BODIPY-$C_{12}$ uptake into Caco-2 cells. Curves were fit using dose-response nonlinear least-squares regression models in Prism software. (A) compound I-1; (B) compound II-1; (C) compound III-1; (D) compound IV-1; and (E) compound V-1. Values are presented as means±SE for 3-4 experiments assayed in triplicate.

Fatty acids are enigmatic molecules that, on the one hand, are essential for cellular structure, function and signaling and, on the other hand, must be contained or their detergent properties will prove lethal to cells. Mother Nature has, therefore, developed ways to compartmentalize, sequester and regulate the movement of these molecules between and within cells. For example, within the blood stream, free fatty acids (FFA) are buffered and moved by serum albumin, and as complex lipids by the lipoproteins. Within cells, the fatty acid binding proteins serve a similar function for the free carboxylic acids, while fatty acids esterified in highly hydrophobic complex lipid species are partitioned into membranes or sequestered in lipid droplets.

Upon presentation to the cell, fatty acids must be transported across the cell membrane and trafficked to sites of utilization. Generally, the free fatty acid concentration in the extracellular space is extremely low. Therefore, the efficient transport of long-chain fatty acids is expected to require specific membrane-bound and membrane-associated transport systems to accumulate these compounds against a concentration gradient, where the intracellular concentrations of fatty acids are up to two- to three-fold higher than external unbound fatty acid concentrations. Different cell types contain a specific repertoire of membrane-bound and membrane-associated proteins, which are believed to govern fatty acid transport in response to differentiation, hormonal stimulus, or environmental stimulus, including changes in nutritional state, temperature, or oxygen availability.

Specific membrane-bound and membrane-associated proteins have been identified that function in one or more steps in the transport of fatty acids across the membrane. To date, four different membrane-bound or membrane associated proteins have been defined in eukaryotic cells that participate in the transport of exogenous long-chain fatty acids: CD36/fatty acid translocase (CD36/FAT), fatty acid binding protein-plasma membrane-bound (FABPpm), fatty acid transport protein (FATP), and long chain acyl CoA synthetase (Acsl). One of the protein-mediated processes by which fatty acid transport occurs is through vectorial acylation, which involves specific FATP isoforms that function alone or in concert with a long chain acyl-CoA synthetase (Acsl). In this coupled transport mechanism, the exogenous fatty acid is activated by esterification with coenzyme A concomitant with transport.

Fatty acid transport proteins (FATPs) were first identified in functional cloning screens designed to identify proteins that resulted in elevated accumulation of fatty acids. FATPs have a domain architecture similar to the acyl-CoA synthetases, which includes an ATP binding domain and a fatty acid binding domain. Generally, however, the fatty acid signature of FATPs is divergent from the Acsl enzymes involved in activation of long chain fatty acids. In addition to the FATP1, five other related mammalian genes, referred to as FATP2 through FATP6, have been cloned and their proteins characterized. The FATPs differ in expression pattern, tissue distribution and subcellular location. For example, FATP1 is found in muscle and adipose tissue; FATP2 in liver and kidney; FATP3 in liver and testes; FATP4 is relatively ubiquitous in fat metabolizing tissues and skin; FATP5 is exclusive to liver; and FATP6 is exclusive to heart. Each FATP functions in thioesterification of a lipophilic substrate with coenzyme A. FATP2, the target of the screen described herein, was first identified as a very long chain acyl-CoA synthetase, called ACSVL1.

This disclosure describes inhibitors of FATP2, which represent candidates for therapeutic applications involved in inhibiting fatty acid transport mediated through FATP2.

Inhibitors of Fatty Acid Transport Proteins

The inhibitors described herein were identified in a screen using a high throughput screening assay (see, U.S. Pat. No. 7,070,944). The inhibitors identified could be categorized into 5 classes of compounds as shown below. The inhibitory properties of each of these 5 classes of compounds was reversible, none disrupted the barrier function of epithelial cells, and each specifically blocked fatty acid transport without disrupting glucose transport or perturbing cell integrity. Interestingly, these compounds were less effective in blocking fatty acid transport in adipocytes, which express FATP1.

A compound of Formula (I):

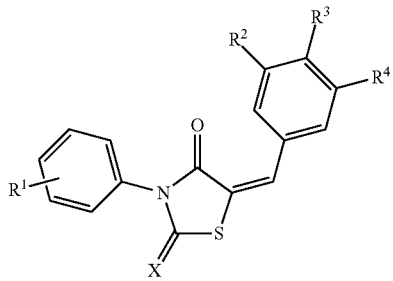

or a pharmaceutically acceptable salt form thereof, wherein:
X is O or S;
$R^1$ is selected from the group consisting of: F, Cl, Br, I, OH, and O($C_{1-6}$ alkyl);
$R^2$, $R^3$, and $R^4$ are independently selected from the group consisting of: H, F, Cl, Br, I, OH, and O($C_{1-6}$ alkyl), wherein at least two of $R^2$, $R^3$, and $R^4$ are not H.

In some embodiments, X is S. In some embodiments, $R^1$ is selected from the group selected from: F, Cl, and O($C_{1-6}$ alkyl). In some embodiments, $R^1$ is $OCH_3$. In some embodiments $R^2$ is selected from H and Br. In some embodiments, $R^3$ is OH. In some embodiments, $R^4$ is O($C_{1-6}$ alkyl). In some embodiments, if $R^1$ is in the para position and is $OCH_3$ and X is S, then $R^2$, $R^3$, and $R^4$ are not H, OH, and OH, respectively. In some embodiments, if $R^1$ is in the meta position and is Cl and X is O, then $R^2$, $R^3$, and $R^4$ are not Br, OH, and $OCH_3$, respectively.

Non-limiting examples of compounds according to Formula (I) include:

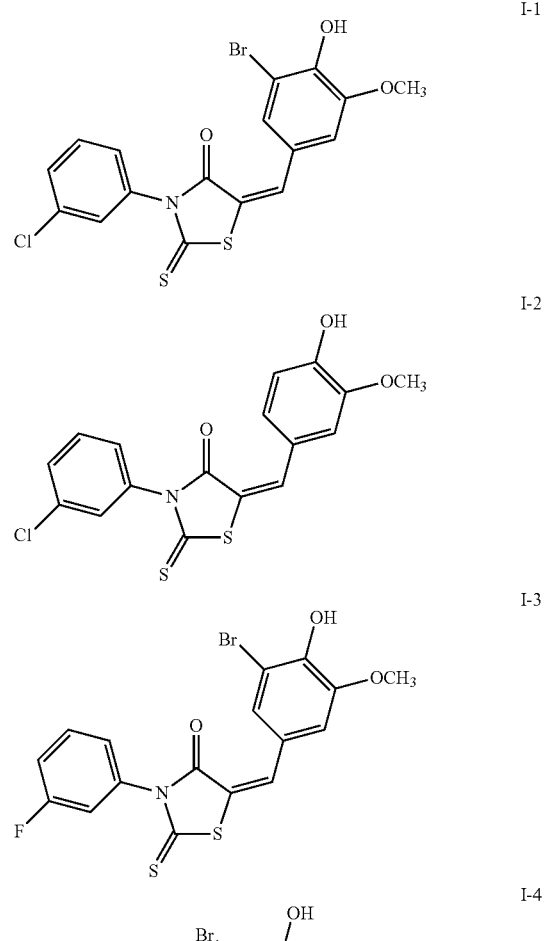

or a pharmaceutically acceptable salt form thereof.

A compound of Formula (II):

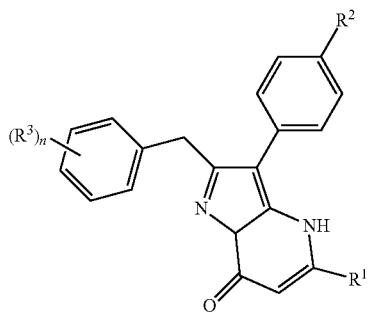

or a pharmaceutically acceptable salt form thereof, wherein:
$R^1$ is H or $NO_2$;
$R^2$ is selected from the group consisting of: H, F, Cl, Br, I, OH, and $O(C_{1-6}$ alkyl);
$R^3$ is selected from the group consisting of: F, Cl, Br, I, OH, and $O(C_{1-6}$ alkyl); and
n is an integer from 0 to 5.

In some embodiments, $R^1$ is $NO_2$. In some embodiments, $R^2$ is selected from the group consisting of: H, Cl, and $O(C_{1-6}$ alkyl). In some embodiments, $R^2$ is $OCH_3$. In some embodiments, n is 0.

In some embodiments, a compound of Formula (II) is a compound according to Formula (IIA):

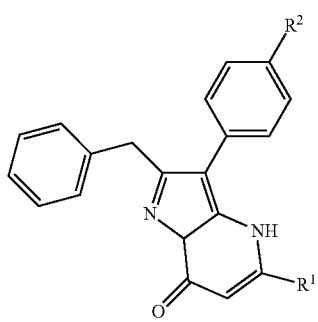

or a pharmaceutically acceptable salt form thereof, wherein:
$R^1$ is H or $NO_2$;
$R^2$ is selected from the group consisting of: H, F, Cl, Br, I, OH, and $O(C_{1-6}$ alkyl).

In some embodiments, $R^1$ is $NO_2$. In some embodiments, $R^2$ is selected from the group consisting of: H, Cl, and $O(C_{1-6}$ alkyl). In some embodiments, $R^2$ is $OCH_3$.

Non-limiting examples of compounds according to Formula (II) and Formula (IIA) include:

II-1

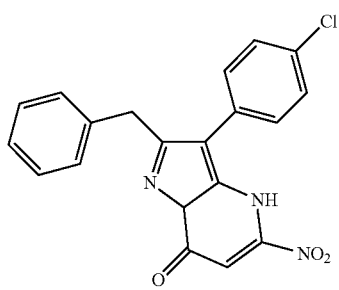

II-2

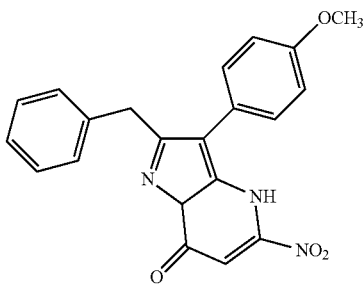

II-3

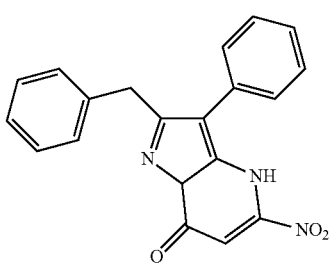

II-4

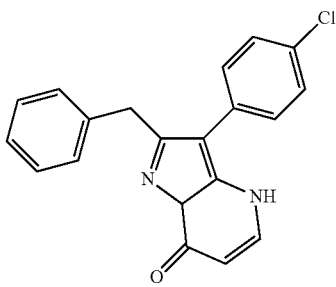

or a pharmaceutically acceptable salt form thereof.

A compound according for Formula (III):

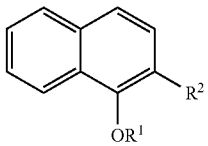

or a pharmaceutically acceptable salt form thereof, wherein:
$R^1$ is H or $O(C_{1-6}$ alkyl); and
$R^2$ is a substituted or unsubstituted heterocycloalkyl or heteroaryl.

In some embodiments, $R^1$ is H. In some embodiments, $R^2$ is a substituted or unsubstituted heterocycloalkyl. In some embodiments, $R^2$ is a substituted or unsubstituted dihydrodiazapine. In some embodiments, if $R^2$ is a substituted pyrazole, $R^1$ is not H.

A non-limiting example of a compound according to Formula (III) includes:

III-1

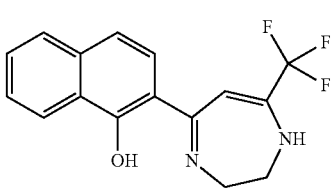

or a pharmaceutically acceptable salt form thereof.

A compound according to Formula (IV):

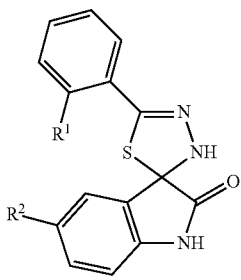

or a pharmaceutically acceptable salt form thereof, wherein:
$R^1$ and $R^2$ are independently selected from the group consisting of: H, F, Cl, Br, I, OH, and O($C_{1-6}$ alkyl).

In some embodiments, $R^1$ is selected from OH and H. In some embodiments, $R^2$ is selected from H and Br.

Non-limiting examples of compounds according to Formula (IV) include:

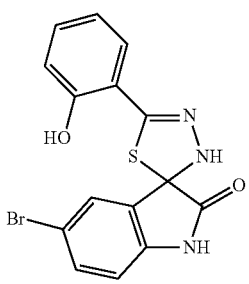
IV-1

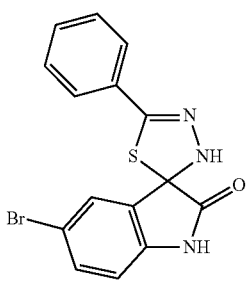
IV-2

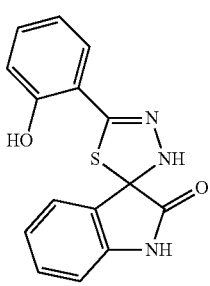
IV-3 or a pharmaceutically acceptable salt form thereof.

A further example of a compound as described herein includes:

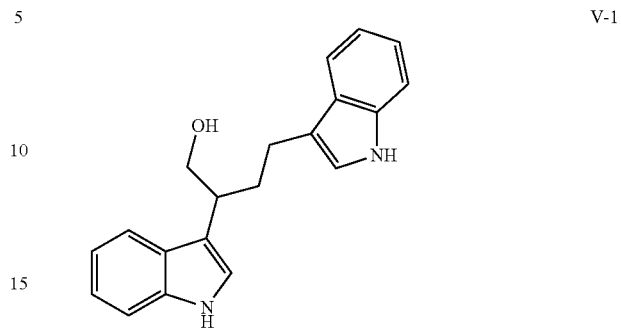
V-1 or a pharmaceutically acceptable salt form thereof.

The term "alkyl" includes straight-chain alkyl groups (e.g., methyl, ethyl, propyl, butyl, pentyl, hexyl, heptyl, octyl, nonyl, decyl, etc.) and branched-chain alkyl groups (isopropyl, tert-butyl, isobutyl, etc.). cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. In certain embodiments, a straight chain or branched chain alkyl has 6 or fewer carbon atoms in its backbone (e.g., $C_{1-6}$ for straight chain, $C_{3-6}$ for branched chain). The term $C_{1-6}$ includes alkyl groups containing 1 to 6 carbon atoms.

The term "heteroaryl" includes groups, including 5- and 6-membered single-ring aromatic groups, that have from one to four heteroatoms, for example, pyrrole, furan, dihydrodiazapine, thiophene, thiazole, isothiaozole, imidazole, triazole, tetrazole, pyrazole, oxazole, isooxazole, pyridine, pyrazine, pyridazine, and pyrimidine, and the like. Furthermore, the term "heteroaryl" includes multicyclic heteroaryl groups, e.g., tricyclic, bicyclic, such as benzoxazole, benzodioxazole, benzothiazole, benzoimidazole, benzothiophene, methylenedioxyphenyl, quinoline, isoquinoline, napthyridine, indole, benzofuran, purine, benzofuran, quinazoline, deazapurine, indazole, or indolizine.

The term "heterocycloalkyl" includes groups, including but not limited to, 3- to 10-membered single or multiple rings having one to five heteroatoms, for example, piperazine, pyrrolidine, piperidine, or homopiperazine.

The term "substituted" means that an atom or group of atoms formally replaces hydrogen as a "substituent" attached to another group. For heteroaryl and heterocyclalkyl groups, the term "substituted", unless otherwise indicated, refers to any level of substitution, namely mono, di, tri, tetra, or penta substitution, where such substitution is permitted. The substituents are independently selected, and substitution may be at any chemically accessible position.

Pharmaceutically acceptable salts of the compounds described herein include the acid addition and base salts thereof.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, hydrogen phosphate, isethionate, D- and L-lactate, malate, maleate, malonate, mesylate, methylsulphate, 2-napsylate, nicotinate, nitrate, orotate, oxalate, palmitate, pamoate, phosphate/hydrogen, phosphate/phosphate dihydrogen, pyroglutamate, saccharate, stearate, succinate, tannate, D- and L-tartrate, 1-hydroxy-2-naphthoate tosylate and xinafoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

A person skilled in the art will know how to prepare and select suitable salt forms for example, as described in "Handbook of Pharmaceutical Salts: Properties, Selection, and Use" by Stahl and Wermuth (Wiley-VCH, Weinheim, Germany, 2002).

The compounds for use in the compositions and methods provided herein may be obtained from commercial sources (e.g., Aldrich Chemical Co., Milwaukee, Wis.) or may be prepared by methods well known to those of skill in the art, e.g., by those methods discussed in standard textbooks such as "Comprehensive Organic Transformations—A Guide to Functional Group Transformations", R C Larock, Wiley-VCH (1999 or later editions). One of skill in the art would be able to prepare all of the compounds for use herein by routine modification of these methods using the appropriate starting materials.

Methods of Using Inhibitors of Fatty Acid Transport Proteins

The five classes of inhibitor compounds described herein can be used to inhibit fatty acid uptake by cells. Such inhibitor compounds can be used to prevent fatty acid transport by cells as a method to limit dietary fat absorption into tissues and organs that are susceptible to the toxic effects of excessive fatty acids (e.g., pancreas, liver and muscle). Thus, these inhibitors are candidates for combating obesity and chronically high blood triglycerides and/or free fatty acids, and can be used to treat a number of diseases associated with dyslipidemias and lipotoxicity in humans or companion animals including, for example, metabolic syndrome, insulin resistant diabetes, cardiovascular disease, stroke, gallbladder disease, non-alcoholic fatty liver disease, osteoarthritis, sleep apnea, respiratory problems and certain cancers (e.g., endometrial, breast and colon).

The compounds described herein intended for pharmaceutical use may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds described herein or in combination with one or more other drugs (or as any combination thereof). Generally, they will be administered as a formulation in association with one or more pharmaceutically acceptable excipients. The term "excipient" is used herein to describe any ingredient other than the compound(s) of the invention. The choice of excipient will to a large extent depend on factors such as the particular mode of administration, the effect of the excipient on solubility and stability, and the nature of the dosage form.

Non-limiting examples of pharmaceutical excipients suitable for administration of the compounds provided herein include any such carriers known to those skilled in the art to be suitable for the particular mode of administration. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β, and γ-cyclodextrin, or chemically modified derivatives such as hydroxyalkylcyclodextrins, including 2- and 3-hydroxypropyl-b-cyclodextrins, or other solubilized derivatives can also be advantageously used to enhance delivery of compounds of the formulae described herein. In some embodiments, the excipient is a physiologically acceptable saline solution.

The compositions can be, in one embodiment, formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers (see, e.g., Ansel Introduction to Pharmaceutical Dosage Forms, Fourth Edition 1985, 126).

The concentration of a compound in a pharmaceutical composition will depend on absorption, inactivation and excretion rates of the compound, the physicochemical characteristics of the compound, the dosage schedule, and amount administered as well as other factors known to those of skill in the art.

The pharmaceutical composition may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular patient, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are, in one embodiment, formulated and administered in unit-dosage forms or multiple-dosage forms. Unit-dose forms, as used herein, refers to physically discrete units suitable for human and animal patients and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrine derivatives, sorbitan monolaurate, triethanolamine sodium acetate, triethanolamine oleate, and other such agents.

Dosage forms or compositions containing a compound as described herein in the range of 0.005% to 100% with the balance made up from non-toxic carrier may be prepared. Methods for preparation of these compositions are known to those skilled in the art. The contemplated compositions may contain 0.001%-100% active ingredient, in one embodiment 0.1-95%, in another embodiment 75-85%.

Pharmaceutical compositions suitable for the delivery of compounds described herein and methods for their preparation will be readily apparent to those skilled in the art. Such compositions and methods for their preparation may be found, for example, in "Remington's Pharmaceutical Sciences", 19th Edition (Mack Publishing Company, 1995).

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Example 1

Materials

Yeast extract, yeast peptone, yeast nitrogen base without amino acids, and dextrose were obtained from Difco (Detroit, Mich.). Complete amino acid supplement and individual amino acids were obtained from Sigma (St. Louis, Mo.). Fatty-acid-free bovine serum albumin (FAF BSA) and other chemical reagents were also obtained from Sigma. The fluorescent long-chain fatty acid analog, 4,4-difluoro-5-methyl-4-bora-3a,4a-diaza-s-indacene-3-dodecanoic acid ($C_1$-BODIPY-$C_{12}$) and the fluorescent glucose analog, 2-(N-(7-nitrobenz-2-oxa-1,3-diazol-4-yl)amino)-2-deoxyglucose (2-NBDG) were purchased from Molecular Probes/Invitrogen (Eugene, Oreg.). Radioactive fatty acid ([$^3$H] oleate; specific activity, 5 mCi/ml) was obtained from Perkin Elmer (Waltham, Mass.). BD Biosciences black with clear bottom 384-well and 96-well microplates were used for primary and secondary screenings in yeast. For Caco-2 and HepG2 cells, tissue culture-treated 96-well black with clear flat bottom polystyrene collagen-coated microplates were obtained from Fisher Scientific (Pittsburgh, Pa.). Transwell® Permeable Supports used for experiments involving Caco-2 cells were obtained from Corning Life Sciences (Acton, Mass.).

Example 2

Cell Culture and Reagents

S. cerevisiae strain LS2086 containing deletions within the FAT1 and FAA1 genes (fat1Δfaa1Δ; MATa ura3 52 his3200 ade2-101 lys2-801 leu2-3,112 faa1Δ::HIS3 fat1Δ::G418) expressing hsFATP2 was used for the primary high throughput screening as detailed previously [Li et al., J. Lipid Res., 2008, 49:230-44; Zou et al., J. Biol. Chem., 2003, 278:16414-22]. For most experiments, yeast minimal medium with dextrose (YNBD) containing 0.67% yeast nitrogen base (YNB), 2% dextrose, adenine (20 mg/L), uracil (20 mg/L), and amino acids as required [arginine, tryptophan, methionine, histidine, and tyrosine (20 mg/L); lysine (30 mg/L); and leucine (100 mg/L)] was used. When a rich medium was required, yeast complete media with adenine (YPDA) was used. Growth in liquid culture and on plates was at 30° C.

The Caco-2 cell line is derived from a human adenocarcinoma and is able to undergo differentiation into polarized epithelial cells that show a brush border phenotype and form well-developed and functional tight junction complexes [Fogh et al., J. Natl. Cancer Inst., 1977, 59:221-6; Grasset et al., Am. J. Physiol., 1984, 247:C260-7]. This cell line is used as an in vitro model to predict human intestinal absorption and secretion [Hilgers et al., Pharm. Res., 1990, 7:902-10]. Caco-2 cells were maintained in Earl's minimal essential medium (MEM) with 20% FBS in a 95% air 5% $CO_2$ atmosphere at 37° C., as previously described [Sandoval et al., Arch. Biochem. Biophys., 2008, 477:363-71]. For growth and differentiation, the BD Biosciences Intestinal Epithelium Differentiation Media Pack was used. Cells were plated in basal seeding medium at a density of $2.5 \times 10^5$ cells/cm$^2$ on a collagen-coated black-clear 96-well plate (BD Biosciences). After 72 h in culture, the basal seeding medium was removed and Entero-STIM medium was added to each well. Both media contained mito-serum extender. After another 24 h, cells were serum-starved for one hour in MEM without phenol red prior to performing the $C_1$-BODIPY-$C_{12}$ uptake assay. HepG2 cells (ATCC, HB-8065) were cultured according to the ATCC protocol. The cells were seeded in 96-well collagen coated plates at a seeding density of $2.5 \times 10^5$ cells/cm$^2$. 3T3-L1 fibroblasts (ATCC, CL-173) were maintained in modified DMEM and 10% BCS. For differentiation into adipocytes, 3T3-L1 cells were treated with methylisobutylxanthine (0.5 mM), dexamethasone (1.0 µM), and insulin (1.75 µM) in DMEM and 10% FBS for 48 hours as described by Student et al. [Student et al., J. Biol. Chem., 1980, 255:4745-50]. After 48 hour incubation with differentiation medium, cells were treated with DMEM and 10% FBS supplemented with insulin (1.75 µM) for 48 hours. Cells were subsequently maintained in DMEM and 10% FBS for an additional 3-6 days until fully differentiated. The number of cells per well in screening trials were determined using the FluoReporter® Blue Fluorometric DNA Quantitation Kit from Invitrogen.

Example 3

Library Descriptions and High Throughput Screening

Two chemically diverse compound libraries were screened using a recently developed live-cell HTS method [Li et al., J. Lipid. Res., 2008, 49:230-44]. The NCI Diversity Set Compound Library comprises 1990 chemical core structures representative of a larger compound library of 140,000 compounds (obtained from NCI's Developmental Therapeutics Program (DTP)). The ChemBridge Corporation compound library includes a diverse, drug-like collection of 100,000 compounds.

For primary screening, LS2086 transformed with the hsFATP2 expression vector (pDB126) or transformed with the empty vector (pDB121) along with the GAL4 transcription factor fusion vector, pRS416Ga14-ER-VP16, [Stafford & Morse, *J. Biol. Chem.*, 1997, 272:11526-34] were pre-grown in YNBD without leucine and uracil (YNBD-leu-ura) as described [Li et al., *J. Lipid Res.*, 2008, 49:230-44]. The cells were subsequently subcultured to $A_{600\,nm}$ of 0.02 in the same medium containing 10 nM β-estradiol to induce FATP2 expression, grown to mid-log-phase (0.8-1.2 $A_{600}$), harvested and then resuspended in PBS to a final density of $6\times10^7$ cells/ml prior to dispensing into a 384-well assay plate (22.5 µl/well; ($1.35\times10^6$ cells)). Wells in the first two rows of each 384-well plate received the vector control cells, and all other wells in the plate received cells expressing hsFATP2. Compounds (2.5 µL) were then added to a final concentration of 40 µM in PBS. After a 2 hr incubation at 30° C., 75 µL of the $C_1$-BODIPY-$C_{12}$ transport mixture (resulting in final concentrations 1.25 µM $C_1$-BODIPY-$C_{12}$, 0.75 µM FAF BSA, 2.1 mM Trypan blue) were added to each well. After 30 min, the cell-associated fluorescence, reflective of fatty acid transport, was measured using a Bio-Tek Synergy HT multidetection microplate reader (Bio-Tek Instruments, Inc. Winooski, Vt.) using filter sets of 485 nm±20 excitation and 528 nm±20 emission. The Z' factor for each plate was calculated using cells expressing hsFATP and vector controls without compound essentially as described [Li et al., *J. Lipid Res.*, 2008, 49:230-44]. A compound was considered a primary hit when the final fluorescence value was three standard deviation units above or below the positive control fluorescence value obtained for each plate assayed. All compounds that resulted in an increase in cell-associated fluorescence were found to be autofluorescent and were not considered further.

Secondary screens were performed to identify compounds that acted non-specifically as described previously [Li et al., *J. Lipid Res.*, 2008, 49:230-44]. Compounds were eliminated from further consideration if (a) they were autofluorescent, (b) were able to quench the BODIPY fluorophore, or (c) permeabilized the cells to allow internalization and quenching of trypan blue. Compounds passing each of these secondary screens were subsequently tested for activity primarily using Caco-2 cells as detailed below.

Example 4

Compound Evaluation in Caco-2 Cells, HepG2 Cells and 3T3-L1 Adipocytes

Caco-2 cells were plated in basal seeding medium at a density of $2.5\times10^5$ cells/cm² in collagen-coated 96-well plates, and differentiated as detailed above. HepG2 cells were cultured in EMEM. Differentiated 3T3-L1 adipocytes were maintained in modified DMEM and 10% FBS. After another 24 h, cells were serum-starved for 1 h in MEM without phenol red prior to performing the $C_1$-BODIPY-$C_{12}$ transport assay [Sandoval et al., *Arch. Biochem. Biophys.*, 2008, 477:363-71; Arias-Barrau et al., *Methods Mol. Biol.*, 2009, 580:233-49]. In a standard reaction, serum-free MEM was removed from the wells and 50 µL of the test compound in MEM (MEM alone for controls) were added to each well and incubation was continued for 1 h. Then 50 µL of $C_1$-BODIPY-$C_{12}$ mixture (final concentrations 5 µM $C_1$-BODIPY-$C_{12}$; 5 µM FAF BSA; 1.97 mM trypan blue) was added to each well, and uptake was allowed to take place for 15 min. Cell-associated fluorescence was measured as detailed above. The inhibition of fatty acid uptake activity using $C_1$-BODIPY-$C_{12}$ was assayed using different concentrations of selected compounds ranging from 0.001 µM to 640 µM. Ligand competition curves were fit by nonlinear least-squares regression using one-site competition and dose-response models and Prism software (GraphPad software, Inc., San Diego, Calif.) in order to determine the compound concentration that reduced $C_1$-BODIPY-$C_{12}$ fluorescence readout by 50% ($IC_{50}$). $K_i$ values were calculated from the $IC_{50}$ using the equation of Cheng and Prusoff as detailed in Li et al. [*J. Lipid Res.*, 2008, 49:230-44] and $K_T$ values published by Sandoval et al. [Sandoval et al., *Arch. Biochem. Biophys.*, 2008, 477: 363-71].

To evaluate if inhibition of fatty acid uptake after compound treatment was reversible, cells were seeded in 96-well plates and treated as described above, but after 1 h the media containing the compound was removed, cells were washed twice with MEM, and fresh media containing serum was added. Cells were incubated 24 h at 37° C. with 5% $CO_2$ and then fatty acid uptake was measured using the standard $C_1$-BODIPY-$C_{12}$ transport assay.

Example 5

Cytotoxicity Assay in Caco-2 Cells

The MTT [3-(4,5-dimethylthiazol-2-yl)-2,5-diphenyltetrazolium bromide] assay was used to determine if compounds of interest were cytotoxic to Caco-2 cells [Mosmann, *J. Immunol. Methods*, 1983, 65:55-63]. Cells were cultured and differentiated as detailed above in collagen-coated 96-well plates. Cells were incubated at 37° C., 5% $CO_2$ for at least one hour and up to 72 h in MEM containing the appropriate dilution of compound. Following this incubation period, the media with compound was removed and 110 µL, of MTT reagent (prepared in MEM (final concentration 0.45 mg/mL MTT)) was added. After a 3 h incubation period, the reaction was terminated by the addition of 150 µL, stop buffer (0.01N HCl in 10% SDS). The plates were incubated for 1 h at 37° C. to facilitate solubilization of formazan crystals; color development was read at $A_{570}$.

Example 6

Long chain Acyl-CoA Synthetase (Acsl) Activity in Caco-2 Cells After Compound Treatment Caco-2 cells were grown and differentiated in 60 mm collagen coated dishes (at a seeding density $2.5\times10^5$ cells/cm²). Following growth and differentiation as detailed above, cells were serum starved for 1 h in MEM and then were treated for 1 h with selected compounds at specified final concentrations. The media was subsequently removed by aspiration and cells washed once with 5 mL PBS, trypsinized using standard procedures and collected by centrifugation. The cell pellet was resuspended in 1 mL STE lysis buffer (10 mM Tris-HCl (pH 8.0); 0.1M NaCl; 1 mM EDTA) and sonicated on ice for 2 min using 3 sec on/off pulses. Samples were clarified by centrifugation (15,000×g, 15 min, 4° C.), the supernatant was transferred to a new tube and assayed for oleoyl-CoA synthetase activity (see below); protein concentrations were determined using the Bradford assay with bovine serum albumin as a standard [Bradford, *Analytical Biochemistry*, 1976, 72:248-54]. In parallel experiments, untreated cells were used to prepare the cell extract for Acsl activity measurements where the compound of interest was added directly to the reaction mixture.

Oleoyl-CoA synthetase activity was determined using a reaction mixture containing 200 mM Tris-HCl (pH 7.5), 2.5 mM ATP, 8 mM $MgCl_2$, 2 mM EDTA, 20 mM NaF, 0.01% Triton X-100, 50 µM [$^3$H]-oleic acid ($C_{18:1}$) (dissolved in 10 mg/mL α-cyclodextrin), and 0.5 mM coenzyme A. Individual enzyme reactions were initiated by the addition of coenzyme A, incubated at 30° C. for 20 min, and terminated by the addition of 2.5 mL of Dole's Reagent (isopropyl alcohol, n-heptane, 1M $H_2SO_4$ (40:10:1) [Dole, J. Clin. Invest., 1956, 35:150-4]. The unesterified fatty acid was removed through organic extraction using n-heptane. Acyl-CoA formed during the reaction remained in the aqueous fraction and was quantified by scintillation counting. Data were expressed as nmol oleoyl CoA formed/min/mg protein.

Example 7

Assessment of the Trans Epithelial Electrical Resistance (TEER)

Caco-2 cells were seeded at a density of $2.5 \times 10^5$ cells/cm$^2$ in a 12-well system using Collagen-Coated Transwell®-COL Inserts (Corning Life Sciences). For growth and differentiation, 100 µL of relevant culture medium was added to the upper compartment and 600 µL was added to the lower compartment of each transwell. To assess integrity of the epithelial barrier after compound treatment, the trans epithelial electrical resistance (TEER) test was used. Confluent and fully differentiated cells were starved of serum for 1 h in MEM without phenol red. Subsequently, 100 µL of MEM containing the selected compound or MEM alone were added to the upper compartment and cells were further incubated 1 h at 37° C., 5% $CO_2$. Trans epithelial electrical resistance was then measured using the Millipore Millicell®-ERS system. For each experiment, background resistance was determined on a transwell insert without cells.

Example 8

Inhibition of Uptake of [$^3$H]-Oleic Acid by Caco-2 Cells After Compound Treatment To assess the inhibition of fatty acid transport using a native fatty acid ligand, 5 µM [$^3$H]-oleate (3.75 µmol/µCi) in 5 µM BSA was added to 60 mm culture dishes containing monolayers of confluent Caco-2 cells differentiated as described above that had been pretreated with the compound of interest for 1 h. The transport reaction was initiated by the addition of [$^3$H]-oleate and incubation was continued for 3 min. Uptake was stopped by the addition of 6 mL of 100 µM BSA prepared in MEM. The stop cocktail was removed by aspiration and cells rinsed once with a solution 50 µM BSA in MEM to eliminate non-transported fatty acid. Cells were trypsinized, scraped from the culture disk and collected by centrifugation (5 min, 1,500×g). The supernatant was discarded and cells were resuspended in 1 mL of MEM. Triplicate aliquots (20 µL) of the cell suspension were used to measure cell-associated radioactivity, which is reflective of fatty acid transport. A cell aliquot of 40 µL, was used to determine the number of viable cells using a bright-line hematocytometer in the presence of 0.4% Trypan blue (w/v). Results were expressed as pmol of fatty acid transported/100,000 cells/3 min. Experiments were repeated at least 3 times.

Example 9

Assessment of Glucose Uptake into Caco-2 Cells

To assess the impact of selected compounds upon glucose transport, Caco-2 cells were seeded and differentiated in 96-well collagen coated plates as detailed above and incubated for 1 h with compound diluted in PBS. Glucose transport was assessed by the addition of 50 µL, of 2-(N-(7-nitrobenz-2-oxa-1,3-diazol-4-yl)amino)-2-deoxyglucose (2-NBDG; final concentration 256 µM) a fluorescent glucose analog [Yamada et al., J. Biol. Chem., 2000, 275:22278-83]. Cells were incubated 30 min at 37° C., 5% $CO_2$ to allow uptake. The medium was removed by aspiration and cells were rinsed once with 100 µL, of PBS. Cell-associated fluorescence was measured using a Bio-Tek Synergy HT multidetection microplate reader using 485±20 nm (excitation), 528±20 nm (emission) filter set.

Example 10

Data Analysis

Values in arbitrary units of the fluorescent signals (AFU) from each HTS plate were acquired using KC4 software in a BioTek Synergy plate reader. These values were exported to Excel (Microsoft Corp., Redmond, Wash.) spreadsheet templates and the assay quality control Z' factor was calculated as described [Li et al., J. Lipid Res., 2008, 49:230-44]. ChemTree software (Golden Helix, Inc., Bozeman, Mont.) was used for additional statistical analysis and to study structure-activity relationships.

Example 11

Results of High Throughput Screening in Humanized Yeast

Using yeast cells in which fatty acid transport was dependent upon hsFATP2, two libraries with over 100,000 chemically diverse compounds were screened for inhibition of fatty acid transport using the fluorescent fatty acid analogue $C_1$-BODIPY-$C_{12}$ [Li et al., J. Lipid Res., 2008, 49:230-44; Li et al., Anal. Biochem., 2005, 336:11-9]. Using a selection criterion of a change in fluorescence of 3 standard deviation units from the mean of untreated control cells, this screen identified 234 compounds as potential inhibitors of fatty acid transport. Of these, 8 were eliminated because they quenched the fluorescent signal of $C_1$-BODIPY-$C_{12}$; another 10 were eliminated because they apparently disrupted the membrane and increased permeability. The remaining 216 compounds were clustered into structural classes using ChemTree (Golden Helix) and JChem (ChemAxon) analysis software. Compounds that were similar in structure to the atypical antipsychotics identified in a previous screening trial were not considered further since compounds of this type may cause hypertriglyceridemia and other metabolic disturbances upon chronic administration in patients [Li et al., J. Lipid Res., 2008, 49:230-44].

Figure 2:
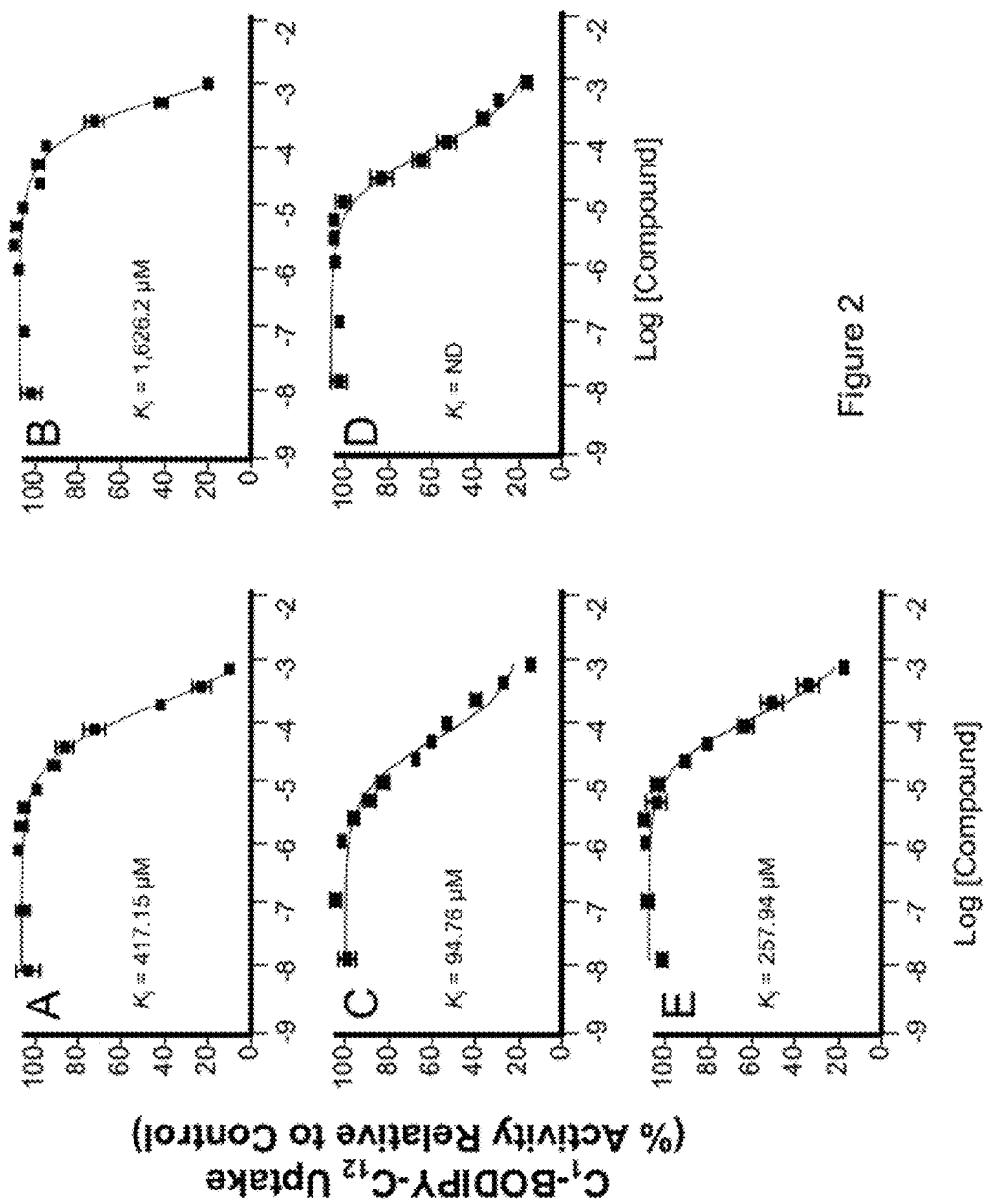
FIG. 2 shows the dose-response curves for the inhibition of $C_1$-BODIPY-$C_{12}$ uptake into 3T3-L1 adipocytes. Curves were fit using dose-response nonlinear least-squares regression models in Prism software. (A) compound I-1; (B) compound II-1; (C) compound III-1; (D) compound IV-1; and (E) compound V-1. Values are presented as means±SE for 4 experiments assayed in triplicate.
Figure 3:
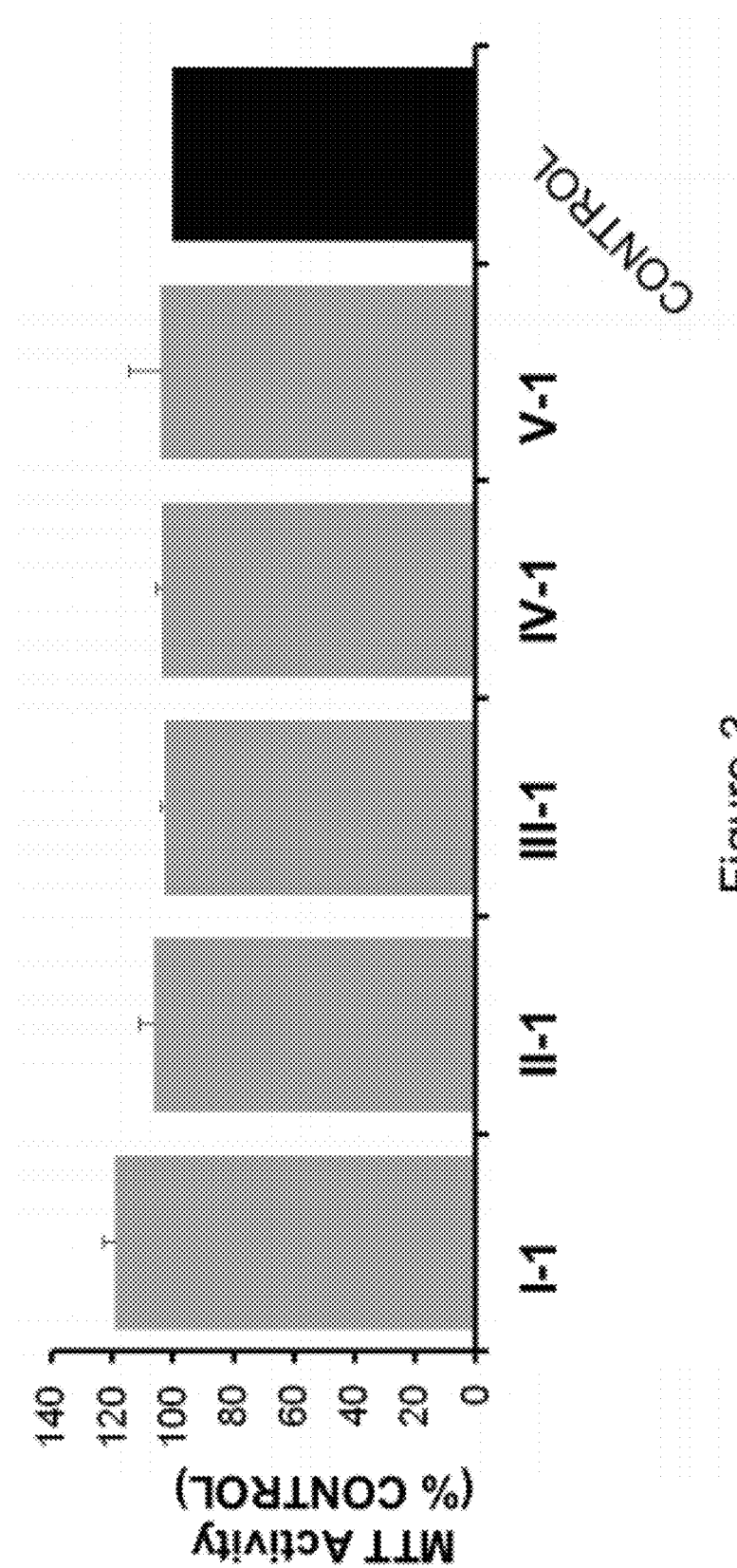
FIG. 3 shows that the selected compounds are not toxic to cells. Caco-2 cells were treated with I-1, II-1, III-1 or IV-1 at 50 µM, or V-1 at 100 µM for 24 h, then the MTT assay was performed to assess mitochondrial function, an indicator of cellular toxicity. Bar height indicates the mean value±standard deviation for 2 experiments assayed in triplicate.

After structural clustering, most compounds fell into 5 structural classes and a representative of each was chosen for extensive characterization in yeast, 3T3-L1 adipocytes, HepG2 hepatocytes and Caco-2 intestinal epithelial cells. Table 1 lists the names and shows the structures of the selected compounds, as well as the $IC_{50}$ for transport inhibition in Caco-2 and HepG2 cells as well as 3T3-L1 adipocytes. These compounds inhibited fatty acid transport in Caco-2 and HepG2 cells at concentrations in the low micromolar range (Table 1) and resulted in sigmoidal dose response curves (FIG. 1). These compounds were not as effective in inhibiting C1-BODIPY-C12 transport in 3T3-L1 adipocytes and resulted in higher $IC_{50}$ values (Table 1, FIG. 2), which may be reflective of the different isoforms of FATP being expressed. When tested in Caco-2 cells, none of the selected compounds resulted in cellular toxicity at 10 times the $IC_{50}$ dosage as measured using the MTT assay (FIG. 3).

TABLE 1

Structure and Activity of Inhibitory Compounds

| Compound Code | Compound ID | Chemical Structure[a] | Caco-2 $IC_{50}$ (μM)[b] | HepG2 $IC_{50}$ (μM) | 3T3-L1 Adipocytes IC50 (μM) |
|---|---|---|---|---|---|
| I-1 | 5584680 | | 3.99 ± 0.32 | 7.55 ± 1.23 | 231.1 ± 33.5 |
| II-1 | 5674122 | | 6.34 ± 0.93 | 10.15 ± 1.26 | 900.9 ± 204.6 |
| III-1 | 6022155 | | 4.93 ± 0.40 | 6.72 ± 0.81 | 52.5 ± 6.7 |
| IV-1 | 5675786 | | 6.66 ± 0.64 | ND | ND |

TABLE 1-continued

Structure and Activity of Inhibitory Compounds

| Compound Code | Compound ID | Chemical Structure[a] | Caco-2 IC$_{50}$ (μM)[b] | HepG2 IC$_{50}$ (μM) | 3T3-L1 Adipocytes IC50 (μM) |
|---|---|---|---|---|---|
| V-1 | 372127 | | 29.22 ± 3.64 | 84.12 ± 14.12 | 142.9 ± 22.4 |

[a]Systematic Names:
I-1, (5E)-5-[(3-bromo-4-hydroxy-5-methoxyphenyl)methylene]-3-(3-chlorophenyl)-2-thioxothiazolidin-4-one;
II-1, 2-benzyl-3-(4-chlorophenyl)-5-(4-nitrophenyl)-1H-pyrazolo[5,1-b]pyrimidin-7-one;
III-1, 2-[7-(trifluoromethyl)-2,3-dihydro-1H-1,4-diazepin-5-yl]naphthalen-1-ol;
IV-1, 5'-bromo-5-(6-oxocyclohexa-2,4-dien-1-ylidene)spiro[1,3,4-thiadiazolidine-2,3'-1H-indole]-2'-one; and
V-1 2,4-bis(1H-indol-3-yl)butan-1-ol
[b]Values are the averages of 3 experiments plus and minus the standard error of the mean.
ND, not determined

Example 12

Reversibility of Selected Compound Action on Fatty Acid Transport

Whether or not inhibition of fatty acid transport was reversible was evaluated by incubating Caco-2 cells with a test compound for one hour, rinsing the cells with MEM and replacing the culture media. After a 24 hour recovery period, fatty acid uptake returned to essentially the pretreatment levels (Table 2). Further characterization was aimed at confirming specific hsFATP mediated fatty acid transport inhibition by these different compounds.

TABLE 2

Compound Inhibition is Reversible

| Compound[a] | % Transport Standard Assay[b] | % Transport after 24 Hour Recovery |
|---|---|---|
| Control (no compound) | 100 | 100 |
| I-1 | 46 ± 3 | 93 ± 13 |
| II-1 | 54 ± 1 | 88 ± 18 |
| III-1 | 35 ± 1 | 74 ± 12 |
| IV-1 | 27 ± 1 | 99 ± 16 |
| V-1 | 52 ± 2 | 99 ± 16 |

[a]All compounds added at f.c. 40 μM to Caco-2 cells
[b]Numbers are the mean of 3-5 experiments ± the standard deviation

Example 13

Figure 4A:
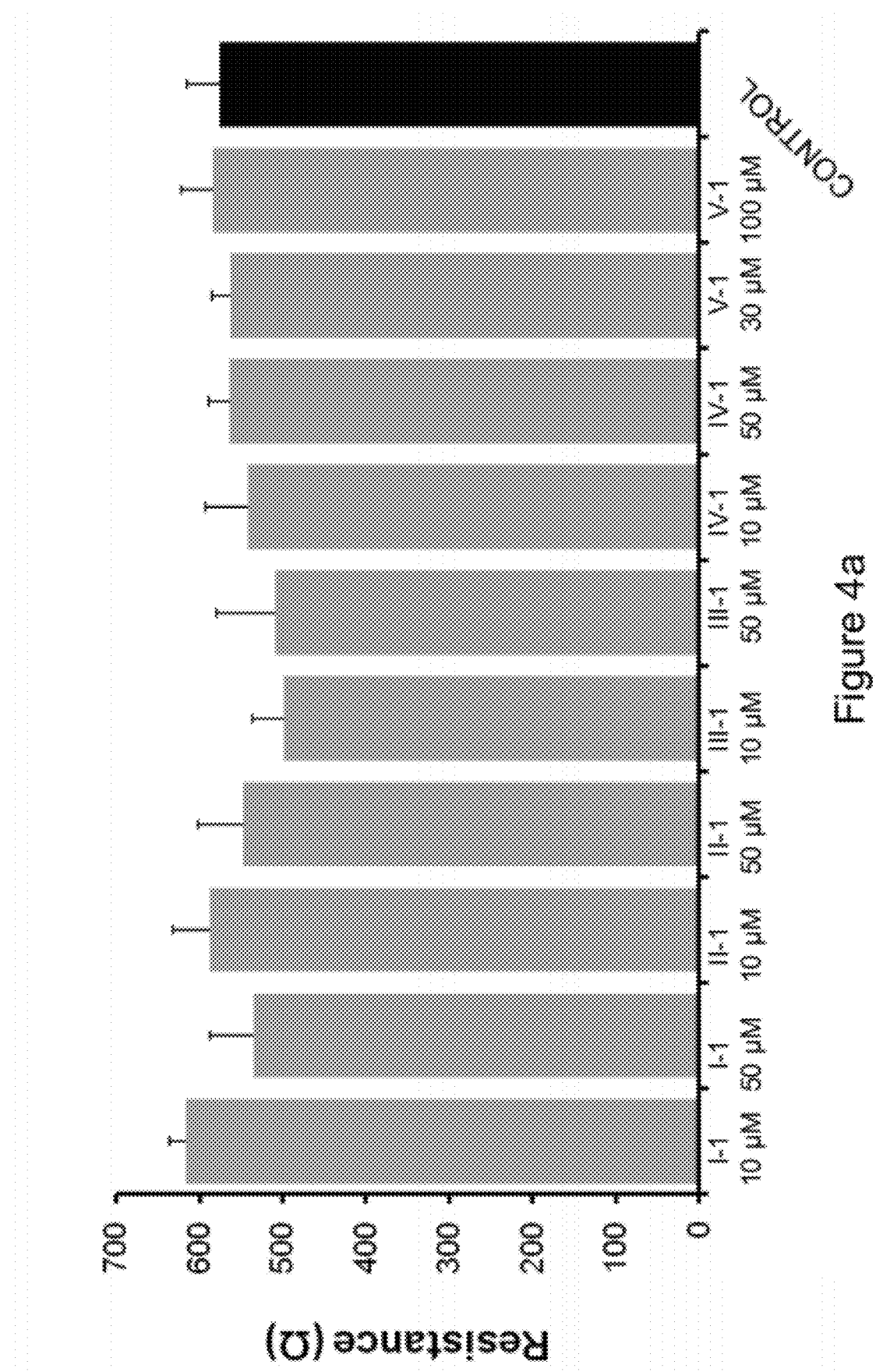
FIG. 4 shows the evaluation of barrier and membrane function of Caco-2 cells after compound treatment. (A) Transepithelial electrical resistance (TEER) was measured in fully differentiated Caco-2 cells after one hour treatment with two different concentrations of selected compounds as shown. Caco-2 cells were seeded and differentiated in Collagen-Coated Transwell®-COL Inserts. TEER was measured using a Millipore Millicell®-ERS device. (B) Transport of the glucose analogue 2-NBDG was measured in Caco-2 cells seeded and differentiated in 96-well plates. Final concentrations of compounds were 20 µM for compounds I-1, II-1, III-1 and IV-1; and 50 µM for compound V-1. Bar height indicates mean values±standard deviation for 3-5 independent experiments assayed in duplicate (A) and triplicate (B), respectively.

Inhibition of Fatty Acid Transport Was Not Due to Nonspecific Effects on the Membrane It was a concern that treatment with a compound might have adverse effects on membrane barrier function by altering, for example, membrane lipid or protein composition. To test if this might be the case, the trans epithelial electrical resistance (TEER) was evaluated in Caco-2 cells treated with each of the compounds. None of the compounds caused a significant (p<0.05) change in membrane permeability by this test (FIG. 4A).

Figure 4B:
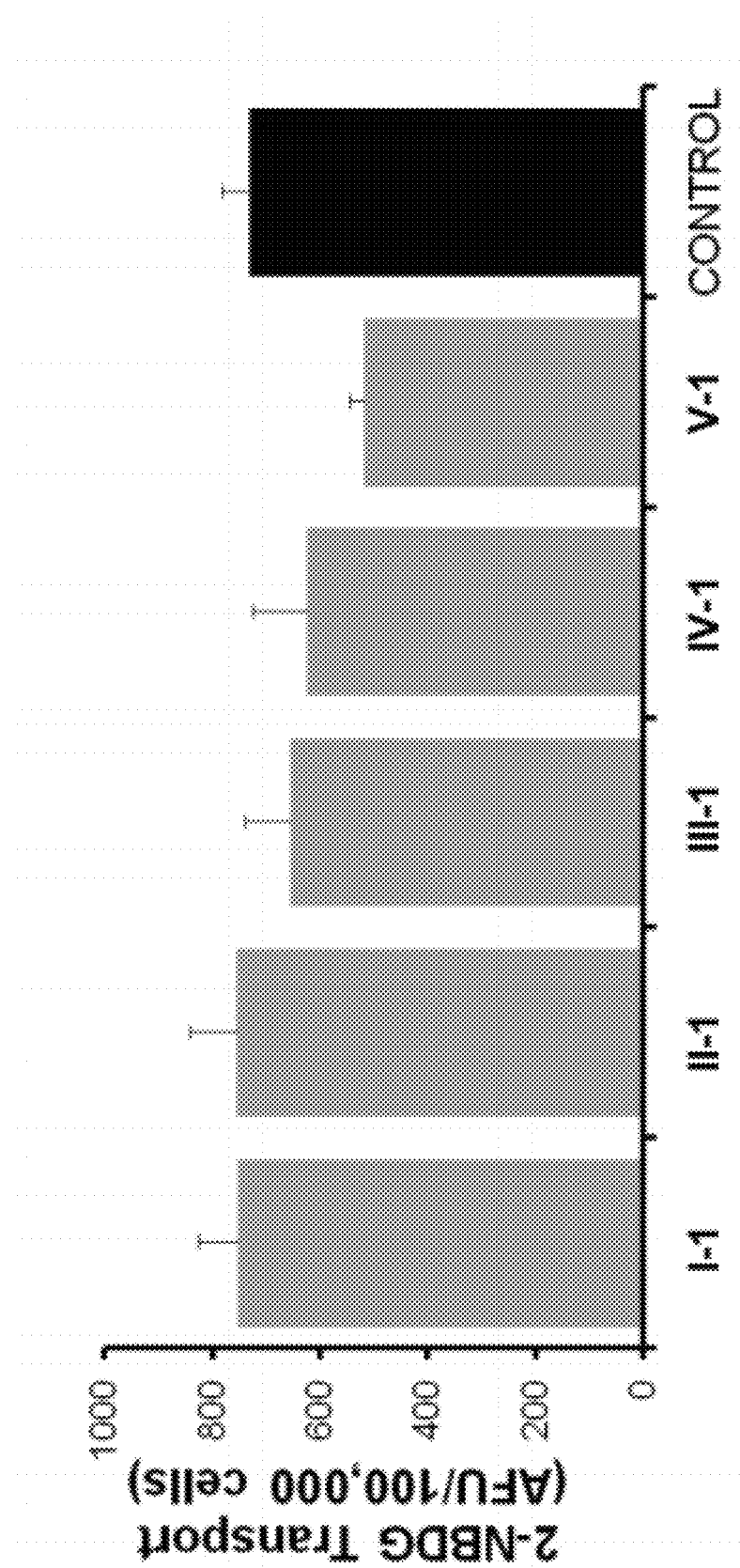

To evaluate whether other membrane specific processes were disrupted, the transport of the fluorescent glucose analogue, 2-NBDG, into differentiated Caco-2 cells was measured following incubation with the selected compounds. Glucose transport was not affected by compounds I-1, II-1, III-1 or IV-1 at 20 μM, a dosage that maximally inhibits $C_1$-BODIPY-$C_{12}$ transport. V-1 at 50 μM reduced 2-NBDG transport slightly (FIG. 4B).

Example 14

Inhibition of the Transport of Native Fatty Acids

Figure 5:
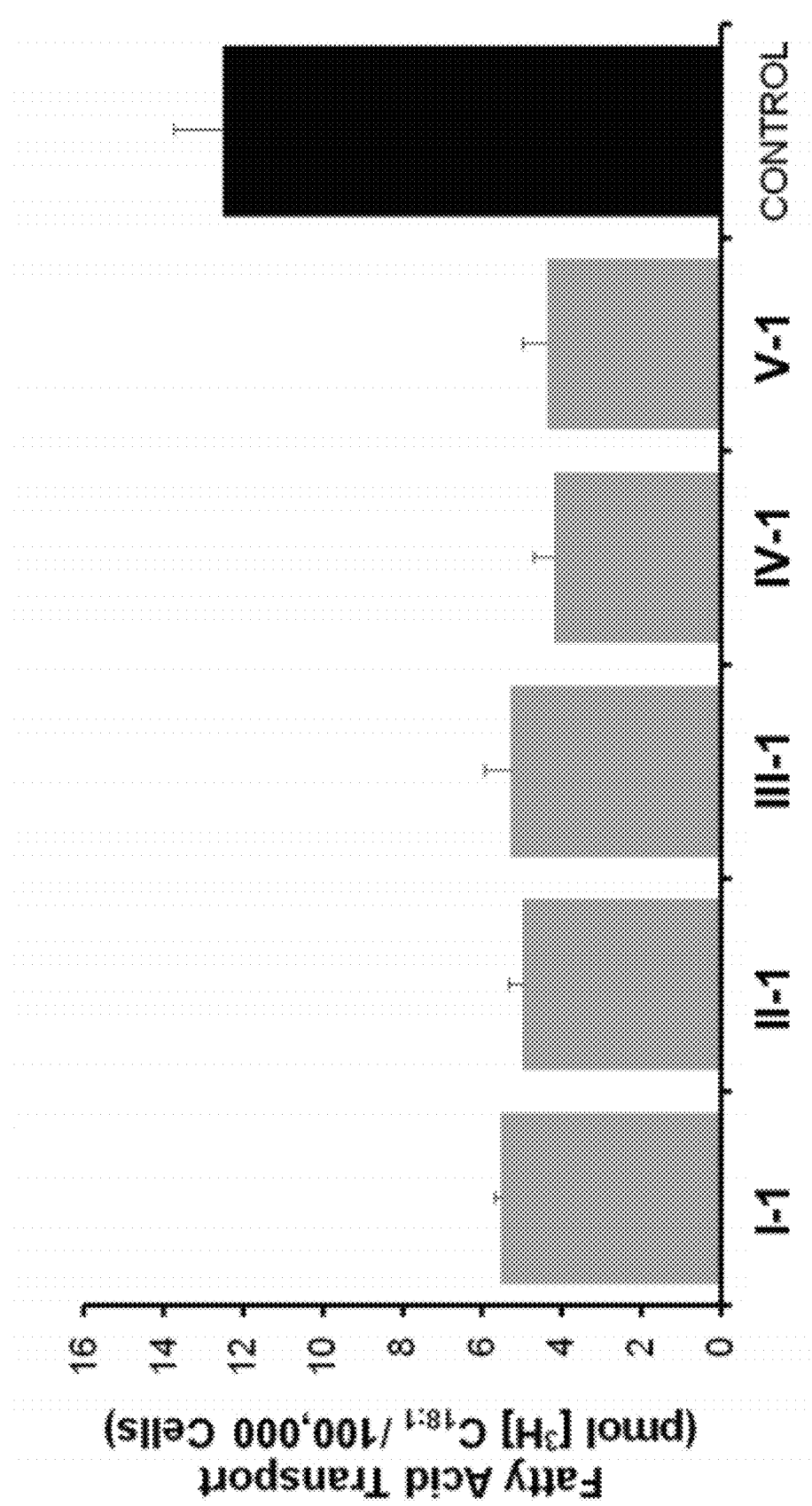
FIG. 5 shows the inhibition of uptake of $[^3H]C_{18:1}$ into Caco-2 cells. Caco-2 cells were preincubated for one hour with selected compounds (final concentrations were 20 µM for compounds I-1, II-1, III-1 and IV-1; and 50 µM for compound V-1) followed by the addition of $[^3H]C_{18:1}$ for 3 minutes as detailed in the text. Bar height indicates the mean values±standard deviation for 3-5 independent experiments.

The fluorescent fatty acid analogue $C_1$-BODIPY-$C_{12}$ is transported and metabolized in a manner similar to the natural fatty acids [Li et al., *J. Lipid Res.*, 2008, 49:230-44; Sabah et al., *Exp. Eye Res.*, 2005, 80:31-6]. However, there is always the concern the three fused rings of the BODIPY moiety that do not occur in natural fatty acids might interact with the fatty acid transport apparatus in a manner that is distinct from the native ligands. Therefore, fatty acid transport into cells was measured using radioactively labeled oleate ([$^3$H]-$C_{18:1}$). The transport of [$^3$H]-$C_{18:1}$ was linear within the first 5 minutes following initiation of the experiment. To test inhibition by the identified fatty acid transport inhibitors, differentiated Caco-2 cells were treated with the selected compounds for 1 hour and measured fatty acid transport using [$^3$H]-$C_{18:1}$ over a 3 minute period. As shown in FIG. 5, the transport of oleate, a representative native fatty acid ligand, was significantly inhibited by all 5 compounds (p<0.01). These observations corroborate results obtained using $C_1$-BODIPY-$C_{12}$ to monitor fatty acid transport and inhibition.

Example 15

AcsI Activity Remained Unchanged Following Compound Treatment

Figure 6:
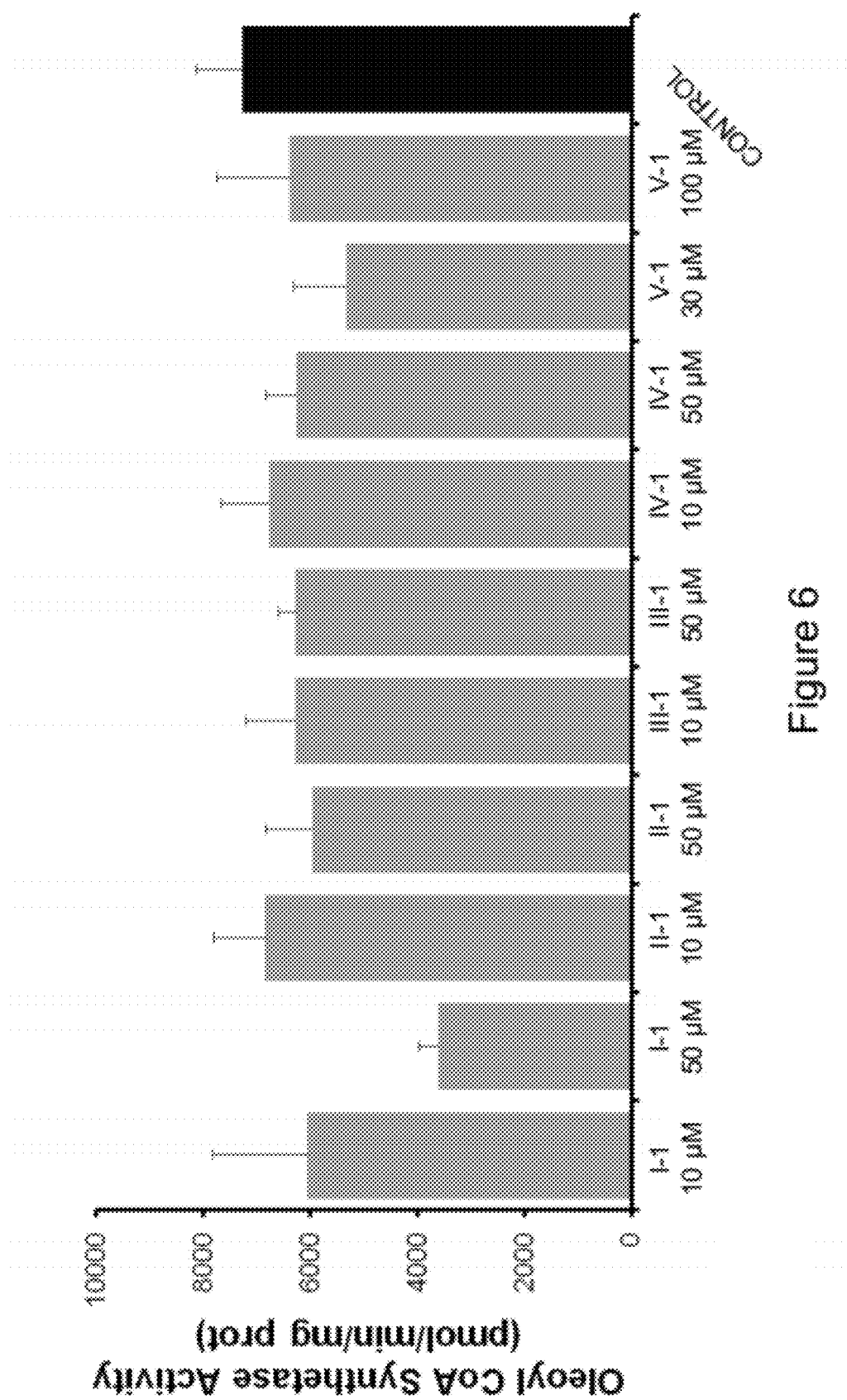
FIG. 6 shows the assessment of oleoyl ($C_{18:1}$)-CoA synthetase activity after compound treatment. Cells were treated for 1 h at the indicated final concentration, then cell extracts were prepared and Acsl activity measured. Bar height indicates mean values±standard deviation for 3-5 independent experiments assayed in duplicate.

Upon entry into a cell, fatty acids are activated to CoA thioesters by acyl-CoA synthetase (AcsI) in order to enter lipid metabolic pathways. It has been shown in yeast that both FATP and AcsI are required for fatty acid transport through the process of vectorial acylation [Faergeman et al., *J. Biol. Chem.*, 2001, 276:37051-9; Faergeman et al., *J. Biol. Chem.*, 1997, 272:8531-8]. As the small compound inhibitors were selected using a live cell assay, there remained the possibility that AcsI, as opposed to hsFATP2, was the target, thereby blocking fatty acid transport. To address whether AcsI was the target of the selected compounds, differentiated Caco-2 cells were pretreated with a compound for 1 hour, the compound was removed by rinsing, and then oleoyl CoA synthetase activity was assayed in total cell extracts. Oleoyl CoA synthetase activity was not reduced by treatment with II-1, III-1, IV-1, or V-1 (FIG. 6). I-1, on the other hand, at 50 µM (10 times the $IC_{50}$), inhibited activity by about 50%. Similar results were obtained when the compounds were added to cell extracts rather than whole cells.

Example 16

Comparison of the Activities of Structurally Related Compounds

To test structural features important in inhibition of fatty acid transport by the selected compounds, fatty acid transport inhibition of related compounds available from the ChemBridge compound database was next addressed. The structures can be found in Table 3, and the predicted chemical properties can be found in Table 4. Five compounds similar to I-1 were evaluated, and most were 50 to 100 times less potent than the parent compound (Table 3). One compound, I-4, had an $IC_{50}$ similar to I-1. The only difference between I-1 and I-4 is that I-4 contains a fluorine on the R1 phenolic ring while I-1 contains a chlorine in that position. Replacing the sulfur with oxygen at position R2 increases the $IC_{50}$ by 25- to 126-fold. The positions of the methyl ether, hydroxyl and Br on the R3 phenolic ring in I-1 and I-4 are identical and likely contribute to the ability to block fatty acid transport with comparable efficiency. Three related compounds similar to II-1 were tested and it was found that the nitrite at position R1 appears to have an influence on activity at therapeutic levels (Table 3B). Only one compound similar to III-1, III-2, was tested, and it was nearly 50-fold less effective (Table 3C). The R groups differ considerably between III-1 and III-2 and, thus, fewer conclusions can be made regarding functional groups that disrupt fatty acid transport. Two additional compounds related to IV-1 were tested next and it was found that both had $IC_{50}$s in the same range as IV-1 (Table 3D). Thus, the bromine at position R2 appears to be more important to impart activity as opposed to the hydroxyl at position R1.

TABLE 3

Analysis of compounds structurally related to I-1, II-1, III-1 and IV-1 in Caco-2 cells

| Compound | R1 | R2 | R3 | $IC_{50}$ (µM) |
|---|---|---|---|---|
| A. Formula (I) compounds | | | | |
| I-1 | 3-Cl-phenyl | S | 2-Br-4-OH-5-OCH₃-phenyl | 3.99 ± 0.32 |
| I-2 | 3-Cl-phenyl | S | 4-OH-3-OCH₃-phenyl | 121 ± 25 |
| I-3 | 4-OCH₃-phenyl | S | 3,4-di-OH-phenyl | 468 ± 212 |

TABLE 3-continued
Analysis of compounds structurally related to I-1, II-1, III-1 and IV-1 in Caco-2 cells
| | | | | |
|---|---|---|---|---|
| I-4 | 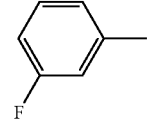 | S | 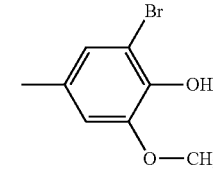 | 4.7 ± 0.8 |
| I-5 | 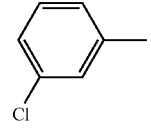 | O | 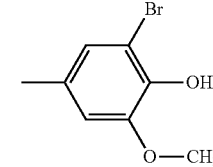 | 504 ± 340 |
| I-6 | 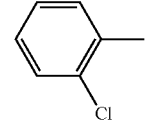 | O | 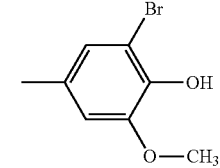 | 102 ± 26 |
B. Formula (II) compounds
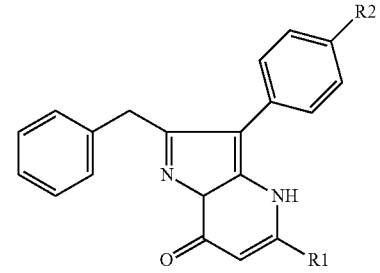
| II-1 | $NO_2$ | Cl | 6.34 ± 0.93 |
|---|---|---|---|
| II-2 | $NO_2$ | $OCH_3$ | 17.3 ± 3.01 |
| II-3 | $NO_2$ | H | 16.4 ± 2.22 |
| II-4 | H | CL | 76.9 ± 15.7 |
C. Formula (III) compounds
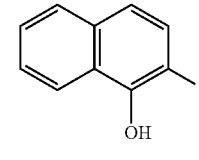
| Compound | R | $IC_{50}$ (μM) |
|---|---|---|
| III-1 | 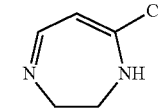 | 4.93 ± 0.40 |
| III-2 | 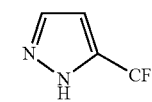 | 241 ± 57 |

TABLE 3-continued

Analysis of compounds structurally related to I-1, II-1, III-1 and IV-1 in Caco-2 cells D. Formula (IV) compounds

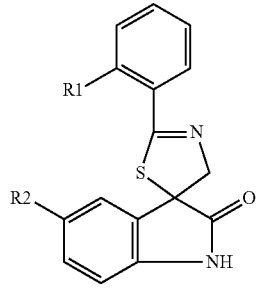

| Compound | R1 | R2 | $IC_{50}$ (μM) |
|---|---|---|---|
| IV-1 | OH | Br | 6.66 ± 0.64 |
| IV-2 | OH | H | 11.9 ± 1.43 |
| IV-3 | H | Br | 4.84 ± 0.69 |

TABLE 4

Chemical properties of selected compounds

| Compound Name/ID | MW | $IC_{50}$ (μM ± SE) | logP | RB | tPSA (Å) | H donor | H acceptor | Rule of 5 violations |
|---|---|---|---|---|---|---|---|---|
| I-1/5584680 | 457 | 3.99 ± 0.32 | 5.45 | 2 | 96.2 | 4 | 4 | 1 |
| I-2/5361510 | 378 | 121 ± 25.4 | 4.28 | 4 | 96.2 | 1 | 4 | 0 |
| I-3/5582711 | 359 | 468 ± 212 | 3.38 | 5 | 105.4 | 2 | 5 | 0 |
| I-4/5674481 | 440 | 4.7 ± 0.82 | 3.39 | 4 | 96.2 | 1 | 4 | 0 |
| I-5/6760222 | 441 | 504 ± 340 | 4.85 | 4 | 81.1 | 1 | 5 | 0 |
| I-6/7140230 | 441 | 102 ± 26.1 | 4.85 | 4 | 81.1 | 1 | 5 | 0 |
| II-1/5674122 | 457 | 6.34 ± 0.93 | 5.7 | 4 | 87.8 | 1 | 5 | 1 |
| II-2/5670982 | 452 | 17.3 ± 3.01 | 5.0 | 5 | 97.1 | 1 | 6 | 0 |
| II-3/5675245 | 422 | 16.4 ± 2.22 | 5.0 | 4 | 87.8 | 1 | 5 | 0 |
| II-4/5679381 | 412 | 76.9 ± 15.7 | 5.8 | 4 | 44.7 | 1 | 3 | 1 |
| III-1/6022155 | 306 | 4.93 ± 0.40 | 2.91 | 2 | 44.6 | 2 | 3 | 0 |
| III-2/6001852 | 278 | 241 ± 57.01 | 3.4 | NA | NA | 2 | 6 | 0 |
| IV-1/5675786 | 376 | 6.66 ± 0.64 | 4.15 | 0 | 69.2 | 3 | 5 | 0 |
| IV-2/5681753 | 297 | 11.9 ± 1.43 | 1.19 | 1 | 73.7 | 3 | 3 | 0 |
| IV-3/5830995 | 360 | 4.84 ± 0.69 | 2.97 | 1 | 53.5 | 2 | 2 | 0 |

Data for IC50 derived from laboratory data. All additional information from PubChem and ChemSpider databases;
RB, rotatable bonds;
tPSA, topological polar surface area;
NA, not available Example 17

Animal Experiments

C57BL/6 female mice (age 8 weeks) are placed on a 60% high fat (lard) diet (TestDiet formula 58G9) for 4 weeks prior to compound administration to allow time for the animals to adjust to the diet, begin to gain weight, and to elevate serum lipid levels. A second diet with the same composition but 12% fat calories is used as a control (TestDiet formula 58G7). The normal fat and calorie diet is also necessary to identify alterations in eating behavior, weight loss or gain, and serum lipid levels apart from the high fat diet regime. The compounds being tested are administered either by gavage or IP injection (each dosage at 5 or 100 mg/kg) once per day for 7 days. The lipase inhibitor, Orlistat (Xenical™), is administered at the same dosage for comparison since this compound is known to inhibit fat absorption. Mice have free access to food and water over the course of the study. Controls include mice receiving vehicle alone and maintained on each diet. Experiments use 3-12 mice per group.

Example 18

Assessment of Compound Treatment on Growth and Overall Health

To evaluate effects due to treatment with the compound, mice are observed visually once per day to verify normal activities and behaviors. Weight is recorded once per week during the preliminary feeding period and then every day once administration of the compound has begun. Food intake is measured periodically during the 4 week pretrial period and daily during the 7 day compound treatment schedule.

Example 19

Measurement of Blood Lipids and Serum Chemistries

Serum lipids are measured using blood samples (obtained from periorbital bleeding of anesthetized animals) on the day the high fat diets are begun, at week 2 and week 5 prior to administration of the first dose of compound, and then again on the last (7th) day of compound treatment. Lipids are extracted from serum samples using Folch extraction method (Folch et al., *J. Biol. Chem.*, 1957, 226:497-509). Triglycerides and cholesterol levels are measured using commercial kits (Wako).

To assess compound effects on liver function, whole blood is drawn by cardiac puncture at the termination of the experiment (50-100 μl) and analyzed using the Mammalian Liver Profile rotor in a VetScan analyzer (Abaxis). This provides data for alanine transaminase (ALT), alkaline phosphatase (ALP), blood urea nitrogen (BUN), albumin (ALB), bile acids (BA), total cholesterol, GGT, and total bilirubin (TBIL).

Example 20

Histological Analysis of Tissues and Measurement of Triglyceride Accumulation To assess whether or not the compounds limit fat deposition in tissues, particularly liver, lipid droplet accumulation is evaluated (Sealls et al., *Biochim. Biophys. Acta*, 2008, 1781: 406-14). C57BL/6 mice in particular are prone to obesity-associated fatty liver and it is expected that the control mice (receiving vehicle alone) on the high fat diet will present this phenotype. For these experiments, at the end of the 7 day compound treatment, animals are sacrificed and necropsies performed. Tissue samples (e.g., liver, soleus muscle, heart, pancreas and adipose) are stored frozen at −80° C. and includes untreated tissues, portions treated with RNAlater® for RNA extraction, portions treated with OCT then snap frozen for Oil red O, and formalin-treated tissues imbedded in paraffin blocks for histology. Sectioning and imaging of tissues is performed by the UNL Center for Biotechnology Microscopy Core Facility. Lipid extraction, quantification and analysis are carried out by standard laboratory procedures.

Example 21

Measurement of Sterol and Fatty Acid Content of Feces

Sterol and fatty acid absorption are studied with respect to compound treatment. For fecal analysis of lipids, animals are individually housed and food and water provided ad libidum. Early in the morning, bedding is changed and then feces are collected after six hours. These experiments are performed prior to initiation of the diets, prior to drug treatment during the 4th week of the diets, and on days 5-7 of compound treatment. Lipids are extracted from fecal samples using Folch extraction methods. Nonadecanoic acid and 5α-cholestane are added as tracers for recovery of fatty acids and sterols, respectively. The samples are split for identification and quantitation of sterols, oxysterols, and fatty acids using routine GC-MS. Bile acids are measured by enzymatic assay employing 3α-hydroxysteroid dehydrogenase. Total triglycerides are measured using a commercially available kit (Wako). Lipid mass is normalized to food consumption and dietary fat content for determination of percent fat absorption.

Example 22

Rate of Uptake of Fatty Acids

Fecal lipid content provides a crude estimate of lipid absorption due to diet and/or compound treatment. To more carefully assess fatty acid absorption, an isotopic tracer method is used. For these experiments, mice are fasted overnight on day 7 and intravenously injected with 500 mg/kg Tyloxapol to block serum lipase activity and to allow serum lipid accumulation to be monitored. Mice are gavaged with 500 μl of an Intralipid Fat Emulsion mixture containing 10 μCi [$^3$H]-triolein. Blood samples (obtained via tail clip) are collected at time zero and every hour after gavage for 4 hours. Mice are sacrificed after the final bleed, and serum radioactivity and triglyceride content determined by scintillation counting of each sample.

Example 23

Uptake of Cholesterol

The fatty acid uptake inhibitors are expected to be specific for fatty acids and are not expected to effect uptake of sterols. To verify this outcome, the fecal dual isotope method is used to assess sterol absorption. Mice fed ad libidum with the high fat or control diets and then treated with the test compound or vehicle will be gavaged on two consecutive days (days 4 and 5 of compound treatment) with 1 μCi [$^{14}$C] cholesterol and 2 μCi [$^3$H] sitosterol. Sitosterol is used as a non-absorbed control sterol. Fecal samples from each mouse are collected for 3 days after the initial dose (days 5, 6 and 7). Lipids are extracted by the standard Folch procedure and then radioactivity is determined by scintillation counting.

Cholesterol uptake is determined as:

$$\% \text{ uptake} = (^{14}\text{C}/^{3}\text{H gavage} - {}^{14}\text{C}/^{3}\text{H fecal})/(^{14}\text{C}/^{3}\text{H gavage}) \cdot 100\%.$$

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. A method of inhibiting fatty acid uptake by cells, comprising:
   contacting said cells with a compound:

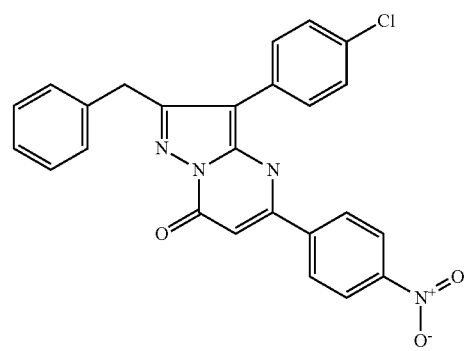 [SMILES: O=c1cc(-c2ccc([N+](=O)[O-])cc2)[nH]c2c(-c3ccc(Cl)cc3)c(Cc3ccccc3)nn12]

or a pharmaceutically acceptable salt form thereof.

2. The method of claim 1, wherein said cells are selected from the group consisting of intestinal epithelial cells and hepatocytes.

3. The method of claim 1, wherein said contacting is in vitro.

4. The method of claim 1, wherein said inhibition is reversible.

5. A method of treating a disease selected from the group consisting of obesity, metabolic syndrome, insulin resistant diabetes, cardiovascular disease, and non-alcoholic fatty liver disease in an individual, comprising:
administering, to said individual, a compound:

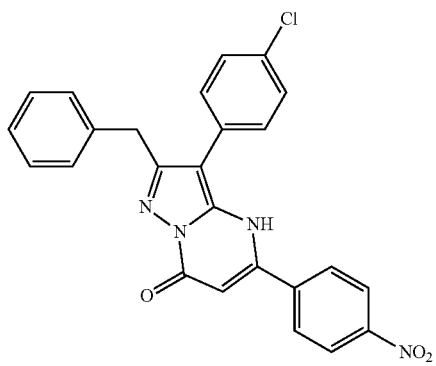 [SMILES: O=c1cc(-c2ccc([N+](=O)[O-])cc2)[nH]c2c(-c3ccc(Cl)cc3)c(Cc3ccccc3)nn12]

or a pharmaceutically acceptable salt form thereof.

6. A method of inhibiting FATP2 in a cell, the method comprising:
contacting said cell with a compound:

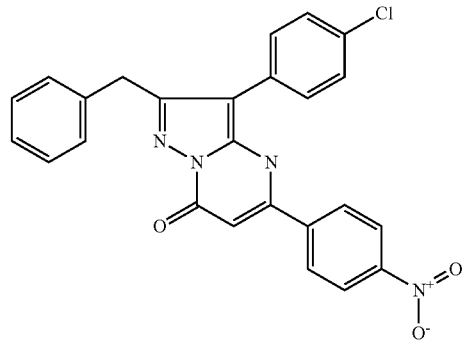 [SMILES: O=c1cc(-c2ccc([N+](=O)[O-])cc2)[nH]c2c(-c3ccc(Cl)cc3)c(Cc3ccccc3)nn12]

or a pharmaceutically acceptable salt form thereof.

7. The method of claim 6, wherein said cell is selected from the group consisting of intestinal epithelial cells and hepatocytes.

8. The method of claim 6, wherein said contacting is in vitro.

9. The method of claim 6, wherein said inhibition is reversible.

* * * * *

UNITED STATES PATENT AND TRADEMARK OFFICE
CERTIFICATE OF CORRECTION

PATENT NO. : 8,410,118 B2
APPLICATION NO. : 13/571632
DATED : April 2, 2013
INVENTOR(S) : Concetta DiRusso and Paul Black Page 1 of 2

It is certified that error appears in the above-identified patent and that said Letters Patent is hereby corrected as shown below:

On the Title Page

Column 1, Line 14 (Other Publications), please delete "Liptocis" and insert -- Lipotoxic --, therefor.

Column 2, Line 44 (Other Publications), please delete " Differentiati3nTg3" and insert -- Differentiating 3T3 --, therefor.

In the Claims

Column 32, Line 53 (Claim 1), please delete

" 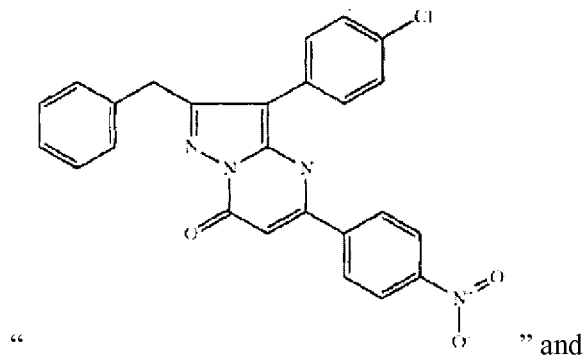 " and insert -- 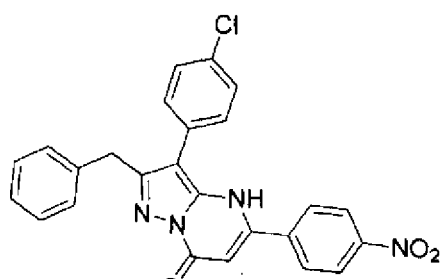 --, therefor.

Signed and Sealed this
Sixteenth Day of September, 2014

Michelle K. Lee
*Deputy Director of the United States Patent and Trademark Office*

CERTIFICATE OF CORRECTION (continued)
U.S. Pat. No. 8,410,118 B2

Column 34, Line 5 (Claim 6), please delete

" 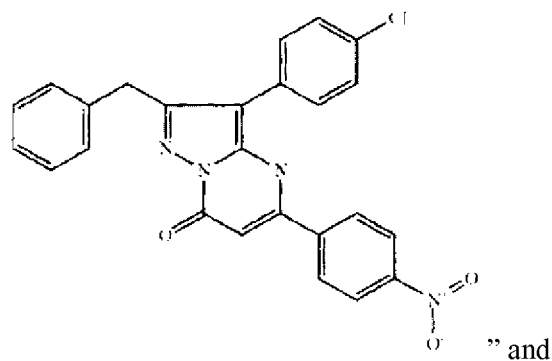 " and insert -- 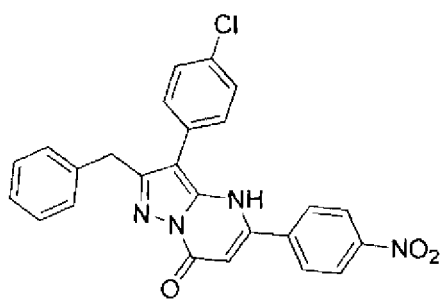 --, therefor.